(12) United States Patent
Kenyon et al.

(10) Patent No.: US 10,940,280 B2
(45) Date of Patent: Mar. 9, 2021

(54) BLOWER

(71) Applicant: ResMed Motor Technologies Inc., Chatsworth, CA (US)

(72) Inventors: Barton John Kenyon, Sydney (AU); David Brent Sears, Woodland Hills, CA (US); Aleksandr S. Nagorny, Canoga Park, CA (US); Michael Bruce Moir, Newbury Park, CA (US)

(73) Assignee: ResMed Motor Technologies Inc., Chatsworth, CA (US)

( * ) Notice: Subject to any disclaimer, the term of this patent is extended or adjusted under 35 U.S.C. 154(b) by 510 days.

(21) Appl. No.: 15/496,030

(22) Filed: Apr. 25, 2017

(65) Prior Publication Data

US 2017/0224940 A1   Aug. 10, 2017

Related U.S. Application Data

(63) Continuation of application No. 14/607,687, filed on Jan. 28, 2015, now Pat. No. 9,662,463, which is a continuation of application No. 13/500,314, filed as application No. PCT/US2010/003010 on Nov. 19, 2010, now Pat. No. 8,973,576.
(Continued)

(51) Int. Cl.
*A61M 16/06* (2006.01)
*A61M 16/00* (2006.01)
(Continued)

(52) U.S. Cl.
CPC .... *A61M 16/0066* (2013.01); *A61M 16/0069* (2014.02); *A61M 16/0605* (2014.02);
(Continued)

(58) Field of Classification Search
CPC .......... A61M 16/0066; A61M 16/0069; A61M 16/0605; A61M 16/0633; A61M 16/0683;
(Continued)

(56) References Cited

U.S. PATENT DOCUMENTS 3,216,413 A   11/1965   Arecheta
3,649,964 A   3/1972   Schoelz
(Continued)

FOREIGN PATENT DOCUMENTS

CN   101018582 A   8/2007
CN   101466429 A   6/2009
(Continued)

OTHER PUBLICATIONS

Extended European Search Report dated Feb. 13, 2018 issued in European Application No. 17206348.9 (7 pages).
(Continued)

*Primary Examiner* — Annette Dixon
(74) *Attorney, Agent, or Firm* — Nixon & Vanderhye P.C.

(57) ABSTRACT

A blower includes a housing including an inlet and an outlet, a stationary component provided to the housing, an impeller positioned between the inlet of the housing and the stationary component, a shield portion including an outer edge substantially aligning with or extending beyond an outer edge of the impeller, and a motor adapted to drive the impeller. The housing and the stationary component cooperate to define a volute that directs air towards the outlet, and the housing includes a separating wall constructed and arranged to divide the volute into a high speed airpath region and a low speed airpath region. The outer edge of the shield portion and the separating wall define a gap between the high speed airpath region and the low speed airpath region.

16 Claims, 33 Drawing Sheets

Related U.S. Application Data

(60) Provisional application No. 61/272,920, filed on Nov. 19, 2009, provisional application No. 61/282,543, filed on Feb. 26, 2010.

(51) Int. Cl.
*F04D 29/42* (2006.01)
*F04D 29/44* (2006.01)
*F04D 29/66* (2006.01)
*A61M 16/10* (2006.01)
*F04D 17/16* (2006.01)
*F04D 25/06* (2006.01)
*F04D 29/28* (2006.01)

(52) U.S. Cl.
CPC ........ *A61M 16/0633* (2014.02); *A61M 16/10* (2013.01); *F04D 17/16* (2013.01); *F04D 25/0693* (2013.01); *F04D 29/281* (2013.01); *F04D 29/4206* (2013.01); *F04D 29/4226* (2013.01); *F04D 29/4233* (2013.01); *F04D 29/441* (2013.01); *F04D 29/665* (2013.01); *A61M 16/0683* (2013.01); *A61M 2205/07* (2013.01); *A61M 2205/42* (2013.01); *A61M 2205/8206* (2013.01); *A61M 2209/088* (2013.01)

(58) Field of Classification Search
CPC .............. A61M 16/10; A61M 2205/07; A61M 2205/42; A61M 2205/8206; A61M 2209/088; F04D 17/16; F04D 25/0693; F04D 29/281; F04D 29/4206; F04D 29/4226; F04D 29/4233; F04D 29/441; F04D 29/665
See application file for complete search history.

(56) References Cited

U.S. PATENT DOCUMENTS

| | | | |
|---|---|---|---|
| 3,727,321 A * | 4/1973 | Waters | A45D 20/18 34/99 |
| 3,738,782 A * | 6/1973 | Fraser | F04D 29/4273 417/423.14 |
| 3,800,431 A * | 4/1974 | Hubner | A45D 20/18 34/99 |
| 3,811,790 A | 5/1974 | Mikulina et al. | |
| 3,831,000 A * | 8/1974 | Waters | A45D 20/18 392/383 |
| 3,969,043 A * | 7/1976 | Bright | F04D 13/06 417/366 |
| 4,019,508 A | 4/1977 | Der Estephanian et al. | |
| 4,233,972 A | 11/1980 | Hauff et al. | |
| 4,297,999 A | 7/1981 | Kitrell | |
| 4,320,755 A | 3/1982 | Flint | |
| 4,430,995 A | 2/1984 | Hilton | |
| 4,478,216 A | 10/1984 | Dukowski | |
| 4,549,542 A | 10/1985 | Chien | |
| 4,590,951 A | 5/1986 | O'Conner | |
| 4,730,612 A | 3/1988 | Dampney | |
| 5,054,480 A | 10/1991 | Bare | |
| 5,104,430 A | 4/1992 | Her-Mou | |
| 5,111,809 A | 5/1992 | Gamble | |
| 5,283,914 A | 2/1994 | James | |
| 5,303,701 A | 4/1994 | Drager | |
| 5,312,465 A * | 5/1994 | Riutta | B01D 46/0049 55/320 |
| 5,318,020 A | 6/1994 | Schegrin | |
| 5,372,130 A | 12/1994 | Stern et al. | |
| 5,378,121 A * | 1/1995 | Hackett | F04D 7/045 417/363 |
| 5,413,097 A | 5/1995 | Birenheide et al. | |
| 5,533,500 A | 7/1996 | Her-Mou | |
| 5,561,862 A | 10/1996 | Flores | |
| 5,671,730 A | 9/1997 | Ollila | |
| 5,720,280 A | 2/1998 | Elstran et al. | |
| 5,868,133 A | 2/1999 | Devries et al. | |
| 6,050,262 A | 4/2000 | Jay | |
| 6,435,184 B1 | 8/2002 | Ho | |
| 6,526,970 B2 | 3/2003 | Devries et al. | |
| 6,561,190 B1 | 5/2003 | Kwok | |
| 6,561,191 B1 | 5/2003 | Kwok | |
| 6,622,311 B2 | 9/2003 | Diaz | |
| 6,705,314 B1 | 3/2004 | O'Dea | |
| 6,752,146 B1 | 6/2004 | Altshuler | |
| 6,772,760 B2 | 8/2004 | Frater et al. | |
| 6,772,762 B2 | 8/2004 | Piesinger et al. | |
| 6,840,735 B2 | 1/2005 | Yaegashi et al. | |
| 6,895,962 B2 | 5/2005 | Kullik et al. | |
| 7,195,014 B2 | 3/2007 | Hoffman et al. | |
| 7,448,383 B2 | 11/2008 | Delache et al. | |
| D589,136 S | 3/2009 | Kenyon | |
| D589,137 S | 3/2009 | Kenyon | |
| D589,138 S | 3/2009 | Kenyon | |
| 7,748,381 B2 | 7/2010 | Croll et al. | |
| 7,913,692 B2 | 3/2011 | Kwok et al. | |
| 8,020,557 B2 | 9/2011 | Bordewick et al. | |
| 8,667,962 B2 | 3/2014 | Kenyon | |
| 8,973,576 B2 * | 3/2015 | Kenyon | A61M 16/0066 128/204.18 |
| 2002/0025253 A1 | 2/2002 | Ozeki et al. | |
| 2002/0029777 A1 | 3/2002 | Zimprich et al. | |
| 2002/0119044 A1 | 8/2002 | O'Conner | |
| 2003/0168064 A1 | 9/2003 | Daly et al. | |
| 2003/0172930 A1 | 9/2003 | Kullik | |
| 2004/0065330 A1 | 4/2004 | Landis | |
| 2004/0079373 A1 | 4/2004 | Mukaiyama et al. | |
| 2004/0226562 A1 | 11/2004 | Bordewick | |
| 2005/0034724 A1 | 2/2005 | O'Dea | |
| 2005/0095151 A1 | 5/2005 | Wampler et al. | |
| 2005/0103339 A1 | 5/2005 | Daly et al. | |
| 2005/0109337 A1 | 5/2005 | Diaz et al. | |
| 2005/0247310 A1 | 5/2005 | Grove et al. | |
| 2005/0217673 A1 | 10/2005 | Daly et al. | |
| 2005/0245860 A1 * | 11/2005 | Britto | A61M 1/066 604/74 |
| 2006/0096596 A1 | 5/2006 | Occhialini et al. | |
| 2006/0150973 A1 | 7/2006 | Chalvignac | |
| 2006/0213516 A1 | 9/2006 | Hoffman | |
| 2006/0237013 A1 | 9/2006 | Kwok et al. | |
| 2007/0008922 A1 | 1/2007 | Abhishek et al. | |
| 2007/0009354 A1 | 1/2007 | Zahuranec et al. | |
| 2007/0095344 A1 | 5/2007 | Abernethy | |
| 2007/0000493 A1 | 6/2007 | Cox | |
| 2007/0247009 A1 * | 10/2007 | Hoffman | F04D 25/0606 310/51 |
| 2007/0251527 A1 | 11/2007 | Sleeper | |
| 2007/0277827 A1 | 12/2007 | Bordewick | |
| 2008/0000474 A1 | 1/2008 | Jochle et al. | |
| 2008/0053438 A1 | 3/2008 | Devries et al. | |
| 2008/0216833 A1 | 9/2008 | Pujol et al. | |
| 2008/0279681 A1 | 11/2008 | Eguchi et al. | |
| 2008/0304986 A1 | 12/2008 | Barton et al. | |
| 2009/0194101 A1 | 1/2009 | Kenyon et al. | |
| 2009/0133698 A1 | 5/2009 | Kuhlman | |
| 2009/0246013 A1 | 10/2009 | Kenyon et al. | |
| 2009/0324435 A1 | 12/2009 | Sears et al. | |
| 2010/0147044 A1 | 6/2010 | Reuss | |
| 2010/0307498 A1 | 12/2010 | Jones et al. | |
| 2012/0199129 A1 | 8/2012 | Kenyon et al. | |
| 2014/0158134 A1 | 6/2014 | Kenyon | |
| 2015/0136140 A1 | 5/2015 | Kenyon et al. | |

FOREIGN PATENT DOCUMENTS

| | | |
|---|---|---|
| DE | 102 61 602 A1 | 7/2004 |
| EP | 0164946 | 12/1985 |
| EP | 0528733 | 8/1992 |
| EP | 1 318 307 | 6/2003 |
| EP | 1655052 | 5/2006 |
| EP | 2085106 | 8/2009 |
| EP | 2 299 121 | 3/2011 |
| FR | 2853838 | 4/2003 |

(56) References Cited

FOREIGN PATENT DOCUMENTS

| | | | |
|---|---|---|---|
| GB | 2209474 | 5/1989 | |
| GB | 2215216 | 9/1989 | |
| JP | 2001-342998 A | 12/2001 | |
| JP | 2004-84602 A | 3/2004 | |
| JP | 2007-113526 A | 5/2007 | |
| TW | 200706197 | 2/2007 | |
| WO | WO 99/13931 | 3/1999 | |
| WO | WO 99/64747 | 12/1999 | |
| WO | WO 2005/016429 | 2/2005 | |
| WO | WO 2005/028009 | 3/2005 | |
| WO | 2006/019323 A1 | 2/2006 | |
| WO | WO 2007/048206 | 5/2007 | |
| WO | PCT/AU2010/001106 | 8/2007 | |
| WO | 2007/117716 A2 | 10/2007 | |
| WO | WO 2007/117716 | 10/2007 | |
| WO | WO 2007/124108 | 11/2007 | |
| WO | WO-2007134405 A1 * | 11/2007 | ........... F04D 17/164 |
| WO | WO 2008/028247 | 3/2008 | |
| WO | WO 2008/108789 | 9/2008 | |
| WO | 2009/026627 A1 | 3/2009 | |
| WO | WO 2010/126383 | 11/2010 | |
| WO | WO 2011/062633 | 5/2011 | |
| WO | 2011/117763 | 9/2011 | |
| WO | WO 2012/113027 | 8/2012 | |

OTHER PUBLICATIONS

Notification of the First Office Action dated May 8, 2019 in Chinese Application No. 201711385173.X, with English translation, 12 pages.

Decision of Rejection dated Sep. 6, 2017 issued in Chinese Application No. 201410483001.6 with English translation (12 pages).

Office Action dated Feb. 27, 2017 issued in Chinese Application No. 201410483001.6 with English translation (14 pages).

Second Office Action issued in a corresponding Chinese Application No. 201410483001.6 dated Aug. 30, 2016 with English language translation thereof.

First Office Action issued in corresponding Chinese Application No. 201410483001.6 dated Apr. 5, 2016 with English language translation thereof.

Email communication dated May 3, 2016 regarding teleconference with Chinese Examiner to correctly list publication No. US 2009/0133698 in search report for First Office Action of Chinese Application No. 201410483001.6 dated Apr. 5, 2016.

International Search Report issued in PCT/US2010/003010, dated Jan. 20, 2011.

Written Opinion of the International Searching Authority issued in PCT/US2010/003010, dated Jan. 20, 2011.

International Search Report issued in PCT/AU2010/001106, dated Dec. 6, 2010.

U.S. Appl. No. 12/794,206, filed Jun. 4, 2010.
U.S. Appl. No. 12/312,042, filed Apr. 23, 2009.
U.S. Appl. No. 12/155,528, filed Jun. 5, 2008.
U.S. Appl. No. 12/310,437, filed Feb. 25, 2009.

4 Photographs of Respironics RemStar blower (no date, admitted prior art).

Office Action issued in corresponding Chinese Appln. No. 201080052431.2 dated Feb. 8, 2014, with English language translation thereof.

Extended European Search Report issued in corresponding Appln. No. 10 831 905.4 dated Oct. 6, 2014.

* cited by examiner

BLOWER

CROSS-REFERENCE TO APPLICATION

This application is a continuation of U.S. application Ser. No. 14/607,687, filed Jan. 28, 2015, now U.S. Pat. No. 9,662,463, which is a continuation of U.S. application Ser. No. 13/500,314, filed Apr. 5, 2012, now U.S. Pat. No. 8,973,576, which is the U.S. National Phase of International Application No. PCT/US2010/003010, filed Nov. 19, 2010, which designated the U.S. and claims the benefit of U.S. Provisional Application Nos. 61/272,920, filed Nov. 19, 2009, and 61/282,543, filed Feb. 26, 2010, each of which is incorporated herein by reference in its entirety.

FIELD OF TECHNOLOGY

The present technology relates to a blower for generating a pressure differential. In an example, the blower may be used in a positive airway pressure (PAP) device used for the delivery of respiratory therapy to a patient. Examples of such therapies are Continuous Positive Airway Pressure (CPAP) treatment, Non-Invasive Positive Pressure Ventilation (NIPPY), and Variable Positive Airway Pressure (VPAP). The therapy is used for treatment of various respiratory conditions including Sleep Disordered Breathing (SDB) and more particularly Obstructive Sleep Apnea (OSA). However, the blower may be used in other applications (e.g., vacuum applications (medical or otherwise)).

BACKGROUND OF TECHNOLOGY

A need has developed in the art for blower designs that are quieter and more compact. The present technology provides alternative arrangements of blowers that consider this need.

SUMMARY OF TECHNOLOGY

An aspect of the disclosed technology relates to a blower including a volute separated into a high speed airpath region and a low speed airpath region.

Another aspect of the disclosed technology relates to a blower including a stationary component structured to support the whole motor and driver assemblies and provide one or more additional functions such as shielding to prevent blade pass tone, bearing tube for bearing retainment and alignment, assist in defining the volute, correct alignment and positioning of the stator assembly, protect or separate the motor from the airpath, and/or central aperture for the shaft or rotor.

Another aspect of the disclosed technology relates to a blower housing including a housing part that provides the inlet and an inlet tube portion aligned with the inlet that is overmolded to the housing part.

Another aspect of the disclosed technology relates to a blower housing including a housing part including a shield to prevent electromagnetic interference of a printed circuit board assembly supported within the housing.

Another aspect of the disclosed technology relates to a seal positioned between the housing and the stationary component of the blower to provide a seal along the volute. In an example, the seal may include structure to support a printed circuit board assembly within the housing and guide wires from the printed circuit board assembly to external the blower.

Another aspect of the disclosed technology relates to a blower in which the stationary component and a stator assembly of the motor are overmolded with one another.

Another aspect of the disclosed technology relates to a blower including a housing including an inlet and an outlet, a stationary component provided to the housing, an impeller positioned between the inlet of the housing and the stationary component, and a motor adapted to drive the impeller. The housing and the stationary component cooperate to define a volute that directs air towards the outlet. The housing includes a separating wall constructed and arranged to divide the volute into a high speed airpath region and a low speed airpath region.

Another aspect of the disclosed technology relates to a blower including a housing including an inlet and an outlet, a stationary component provided to the housing, an impeller positioned between the inlet of the housing and the stationary component, and a motor adapted to drive the impeller. The housing and the stationary component cooperate to define a volute that directs air towards the outlet. The volute includes a high speed airpath region and a low speed airpath region that is radially offset from the high speed airpath region.

Another aspect of the disclosed technology relates to a blower including a housing including an inlet and an outlet, a stationary component provided to the housing, an impeller positioned between the inlet of the housing and the stationary component, and a motor adapted to drive the impeller. The housing and the stationary component cooperate to define a volute that directs air towards the outlet. The volute includes at least one step that extends radially outwardly from the impeller.

Another aspect of the disclosed technology relates to a PAP device including a casing adapted to fit on top of the patient's head in use and a blower provided within the casing. The blower includes an outlet that is angled, curved, and/or oriented towards a lower wall of the casing.

Another aspect of the disclosed technology relates to a blower including a housing including an inlet and an outlet, a motor including a stator assembly, a magnet, and a shaft adapted to cooperatively drive an impeller, and a stationary component provided to the housing. The stationary component may be configured to support the stator assembly of the motor. The stationary component may include a bearing tube adapted to retain one or more bearings. The magnet may be located on a magnet support adapted to align the magnet with the stator assembly. The magnet support may further include a hub that engages with the shaft of the motor to facilitate rotation of the shaft.

Other aspects, features, and advantages of this technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various examples of this technology. In such drawings.

DETAILED DESCRIPTION OF ILLUSTRATED EXAMPLES

Figure 1:
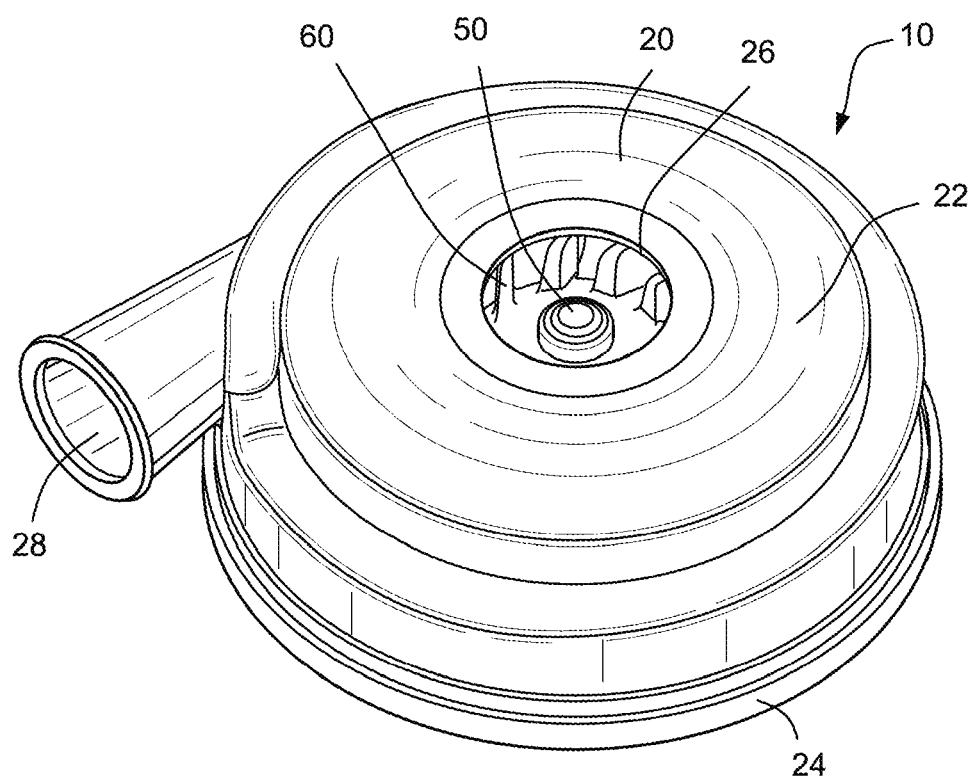
FIG. 1 is a top perspective view of a blower according to an example of the disclosed technology.
Figure 2:
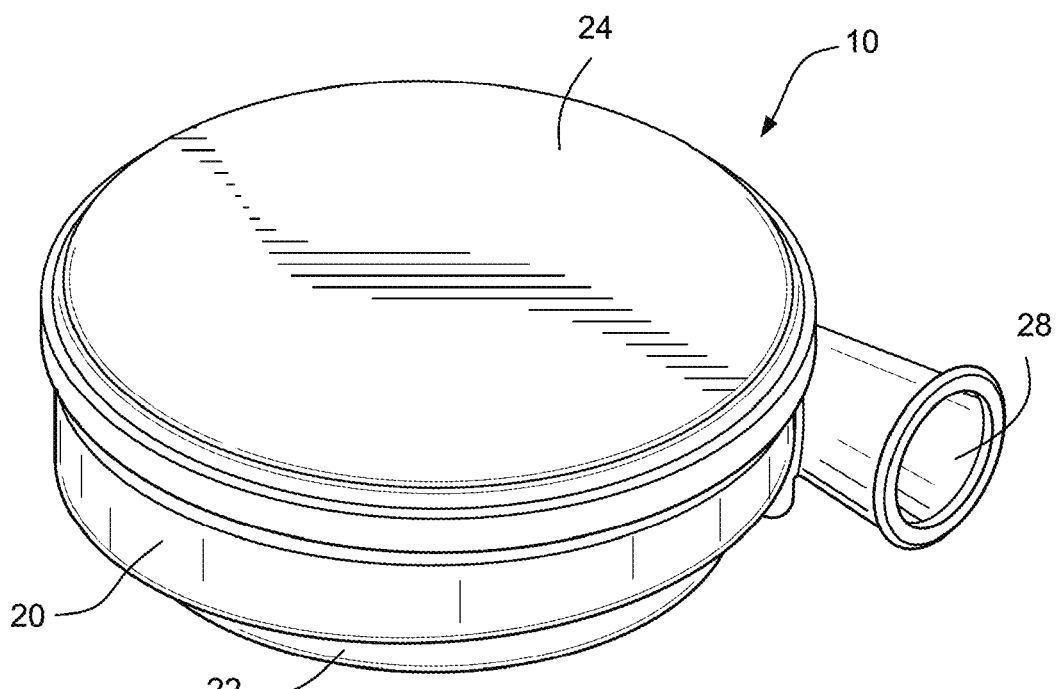
FIG. 2 is a bottom perspective view of the blower of FIG. 1.

The following description is provided in relation to several examples (some of which are illustrated, some of which may not) which may share common characteristics and features. It is to be understood that one or more features of any one example may be combinable with one or more features of the other examples. In addition, any single feature or combination of features in any of the examples may constitute additional examples.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

Aspects of the technology will be described herein in its application to non-invasive ventilation (NIVV) treatment apparatus (e.g., positive airway pressure (PAP) devices), such as CPAP, but it is to be understood that aspects of the technology may have application to other fields of application where blowers are used, e.g., in both positive pressure and negative pressure applications.

In this specification, the words "air pump" and "blower" may be used interchangeably. The term "air" may be taken to include breathable gases, for example air with supplemental oxygen. It is also acknowledged that the blowers described herein may be designed to pump fluids other than air.

Also, each blower example below is described as including a single stage design. However, it should be appreciated that examples of the technology may be applied to multiple stage designs, e.g., two, three, four, or more stages.

Further examples of blowers and aspects related to the present technology are disclosed in PCT Application No. PCT/AU2010/001106, filed Aug. 27, 2010, which is incorporated herein by reference in its entirety.

1. Blower

FIGS. 1-4 illustrate a single stage, centrifugal blower 10 according to an example of the technology. As described below, the blower 10 provides an arrangement that is relatively small, compact, and lightweight. In an example, the blower may be structured to provide pressurized air in the range of 2-30 cmH$_2$O, e.g., 2-15 cmH$_2$O, such as 8 cmH$_2$O, 10 cmH$_2$O and/or 12 cmH$_2$O.

As illustrated, the blower 10 includes a housing 20 (e.g., constructed of metal or plastic, e.g., polycarbonate) with first and second housing parts 22, 24, a stationary component 30 (also referred to as a motor-driver support, a stator component, or an intermediate housing part (e.g., constructed of metal or plastic)), a hub 82 that provides an arm 84 for magnet support and magnetic flux path, a motor 40 positioned within the stationary component 30 and adapted to drive a rotatable shaft or rotor 50, and an impeller 60 (e.g., constructed of plastic such as polycarbonate) provided on one side of the stationary component and coupled to an end portion of the rotor 50. The motor 40 includes stator assembly 44, magnet 42, and rotor 50 as discussed in more detail below.

In an example, a dynamic balancing process may be applied to the rotating masses to minimize noise and vibration during operation. This may be accomplished, for example, by mass removal from two planes, e.g., one plane being at the impeller and another plane being at the hub provided to the rotor. Another way to accomplish this would be to add mass in either of those planes.

1.1 Housing

In the illustrated example, the first housing part 22 provides both an inlet 26 and an outlet 28. The blower is operable to draw a supply of gas into the housing through the inlet and provide a pressurized flow of gas at the outlet. The blower is generally cylindrical with the inlet aligned with an axis of the blower and the outlet structured to direct gas exiting the blower in a generally tangential direction.

1.1.1 Outlet

In the illustrated example, the outlet 28 is in the form of an outlet tube that extends outwardly from the first housing part 22. The shape, size, and/or orientation of the outlet tube may have alternative configurations to modify flow, pressure, etc.

Figure 10:
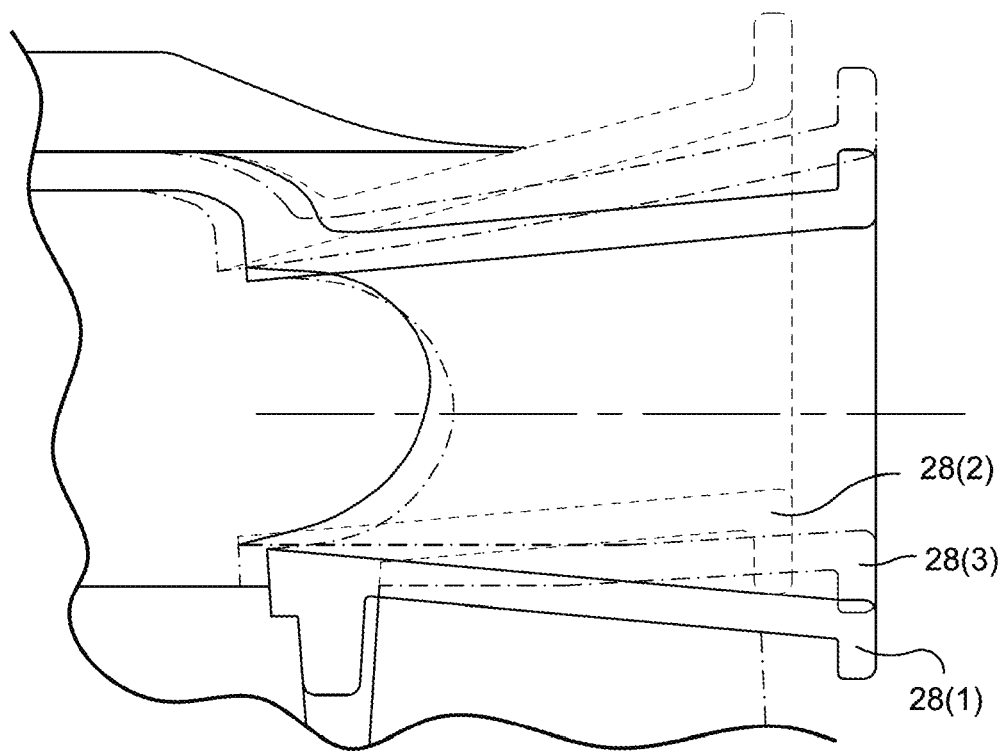
FIG. 10 is a cross-sectional view showing an outlet tube of the blower according to three alternative examples of the disclosed technology.
Figure 11:
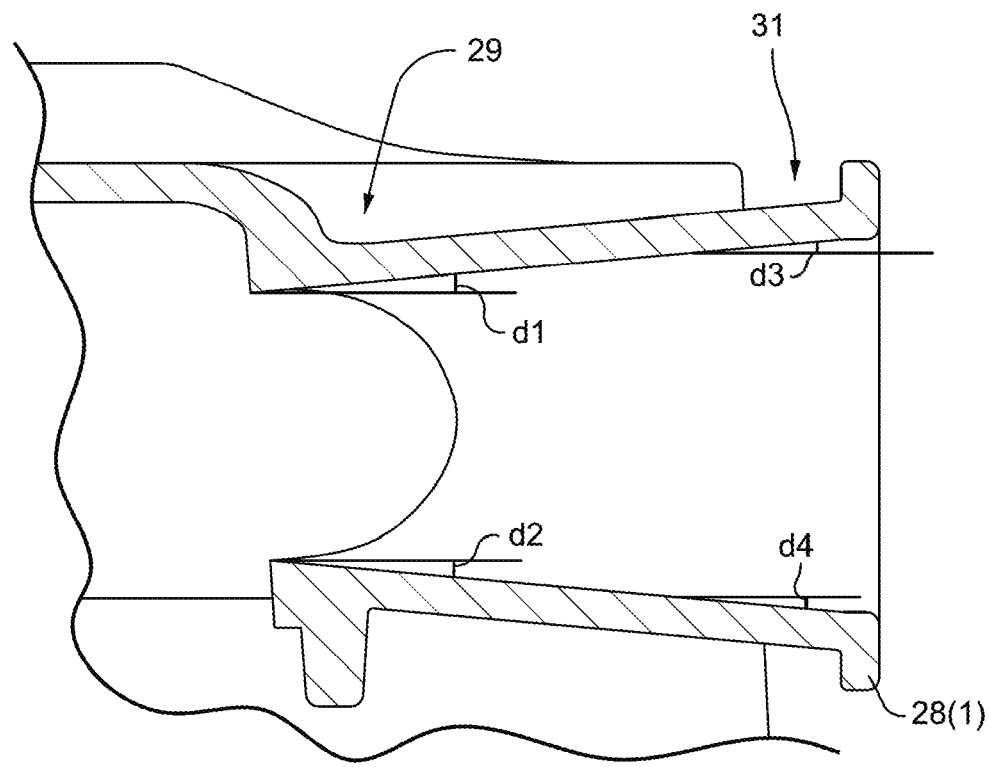
FIG. 11 is a cross-sectional view of one of outlet tubes shown in FIG. 10.
Figure 12:
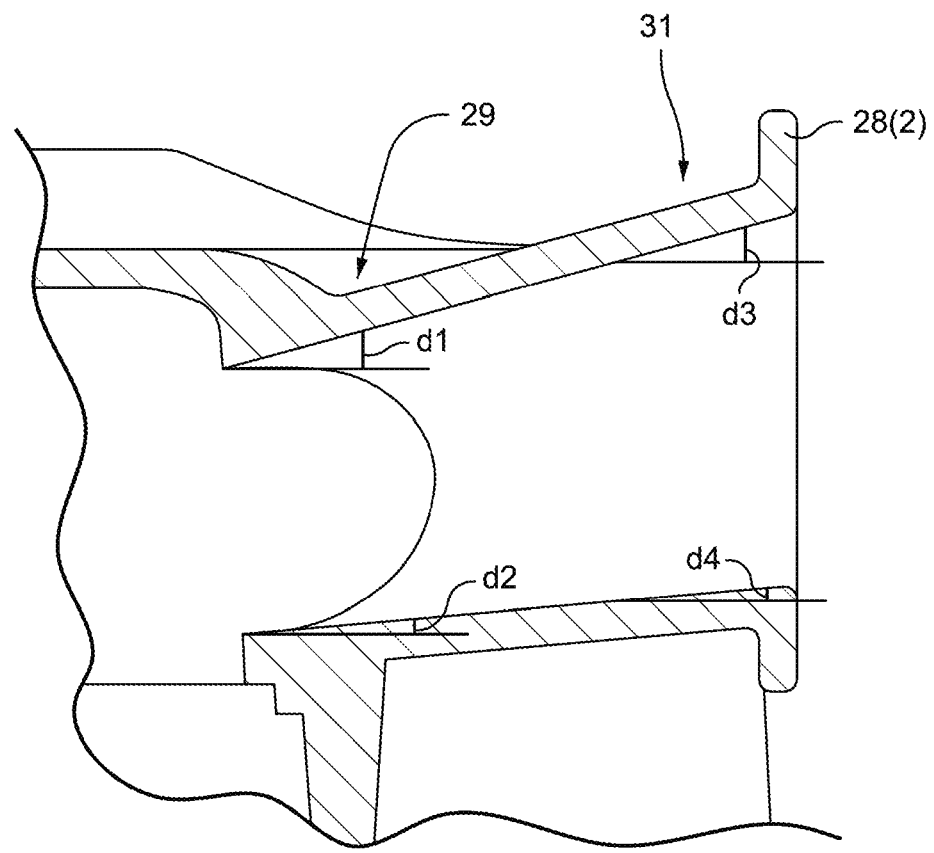
FIG. 12 is a cross-sectional view of another one of outlet tubes shown in FIG. 10.
Figure 13:
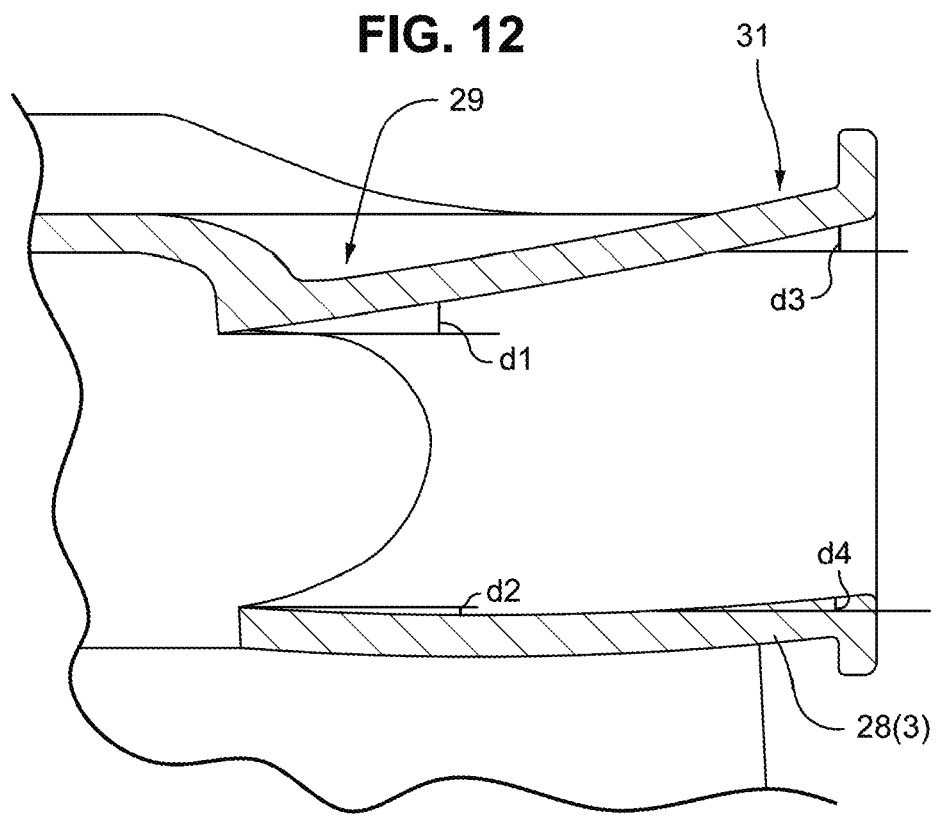
FIG. 13 is a cross-sectional view of another one of outlet tubes shown in FIG. 10.
Figure 14:
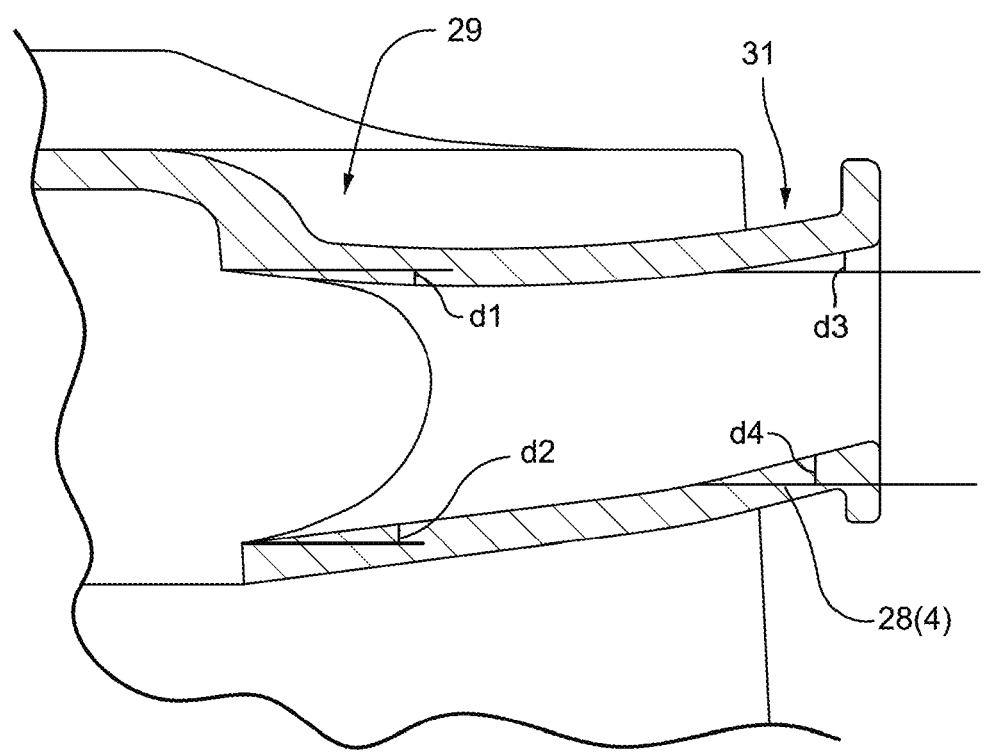
FIG. 14 is a cross-sectional view showing an outlet tube according to another example of the disclosed technology.

For example, FIG. 10 shows three different configurations of the outlet tube 28(1), 28(2), 28(3) in overlapping relation. FIGS. 11 to 13 show the three different configurations in FIG. 10 isolated from one another, and FIG. 14 shows an alternative configuration of the outlet tube 28(4) not shown in FIG. 10.

In each example, the outlet tube diverges from an inlet end 29 of the tube (i.e., the end connected to the main body of the first housing part 22) to an outlet end 31 of the tube. That is, the inlet end 29 defines an internal diameter that is smaller or narrower (e.g., by one or more millimeters) than an internal diameter defined by the outlet end 31. This divergent arrangement decreases the air flow rate so as to provide increased pressure at the outlet end 31 of the tube. Preferably, the divergence of the outlet tube is gradual (i.e., the diameter to the tube does not increase significantly from the inlet end to the outlet end) so as to minimize air turbulence in the tube which may impede pressure and flow.

FIGS. 11-14 show exemplary dimensions of the different configurations of the outlet tube. Although specific dimensions are provided, it should be understood that these dimensions are merely exemplary and other dimensions are possible, e.g., depending on application.

For example, in FIG. 11, the outlet tube 28(1) includes a generally straight orientation with respect to horizontal. In this example, angle d1 at the top of the inlet end 29 is about 5° and angle d2 at the bottom of the inlet end 29 is about −5° which defines an average (center line) of about 0° and a difference (divergence) of about 10°. Angle d3 at the top of the outlet end 31 is about 5° and angle d4 at the bottom of the outlet end 31 is about −5° which defines an average (center line) of about 0° and a difference (divergence) of about 10°. In this example, the minimum slider draft angle for molding may be about 10°.

In FIG. 12, the outlet tube 28(2) includes an angled orientation with respect to horizontal. In this example, angle d1 at the top of the inlet end 29 is about 15° and angle d2 at the bottom of the inlet end 29 is about 5° which defines an average (center line) of about 10° and a difference (divergence) of about 10°. Angle d3 at the top of the outlet end 31 is about 15° and angle d4 at the bottom of the outlet end 31 is about 5° which defines an average (center line) of about 10° and a difference (divergence) of about 10°. In this example, the minimum slider draft angle for molding may be about 10°.

In FIG. 13, the outlet tube 28(3) is curved along its length (e.g., banana-shaped or slight concave shape). In this example, angle d1 at the top of the inlet end 29 is about 6° and angle d2 at the bottom of the inlet end 29 is about −2° which defines an average (center line) of about 2° and a difference (divergence) of about 8°. Angle d3 at the top of the outlet end 31 is about 13° and angle d4 at the bottom of the outlet end 31 is about 5° which defines an average (center line) of about 9° and a difference (divergence) of about 9°. In this example, the minimum slider draft angle for molding may be about 1.7°.

As noted above, the outlet tube 28(3) of FIG. 13 includes a general curved shape, in which the outlet tube is bent or arcuate along its length and the radius of curvature changes along the length. For example, the curvature at the inlet end may be very slight so as to prevent noise and turbulence, and the curvature increases along the length with the maximum curvature provided at the outlet end. The slight bend or no bend at the inlet end of the outlet tube may reduce air turbulence created between the interface of the outlet tube and the pump volute. The reduced turbulence may directly lead to a reduction in pressure drop in the region and a reduction in flow loss, which in turn may lead to improved pumping characteristics of the blower and/or reduced vibration and noise.

Also, the curved outlet tube 28(3) may enable the angle on the air flow exiting the blower to be substantially parallel to the curved surface on the top of the patient's head, when the blower is adapted to be mounted on the crown or in front of the crown of the patients head in use (e.g., see examples below).

Figure 15:
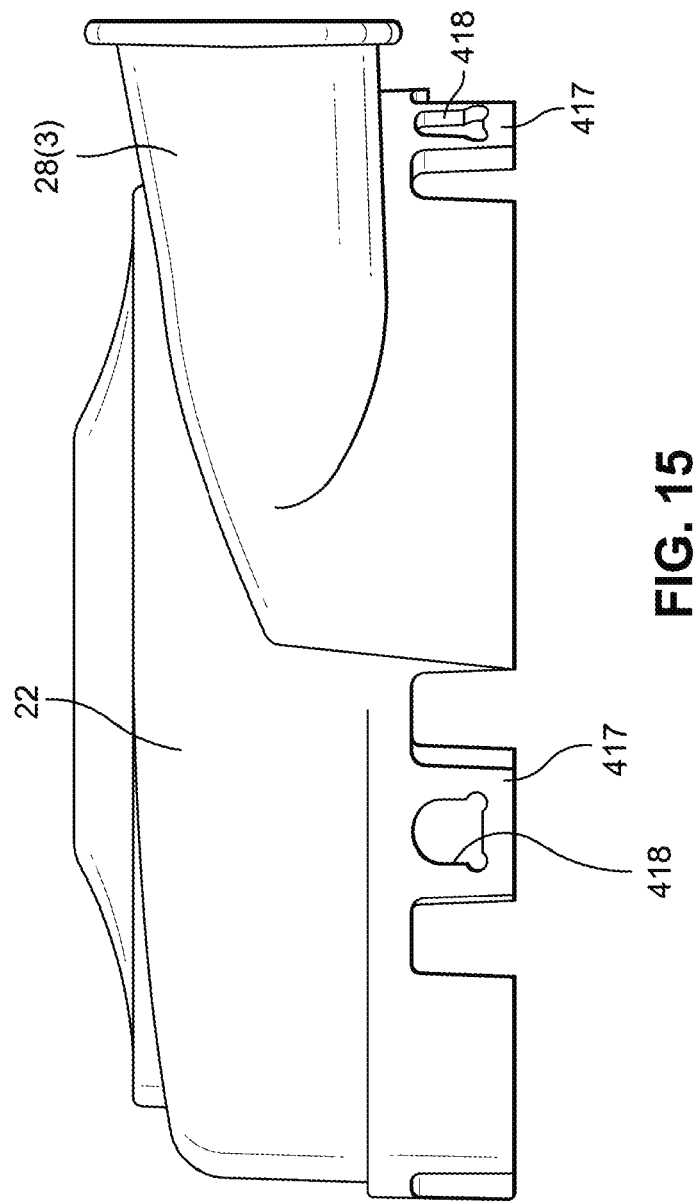
FIG. 15 is a side view of a first housing part including an outlet tube according to an example of the disclosed technology.

FIG. 15 shows another view of the outlet tube 28(3) of FIG. 13 provided to the first housing part 22.

FIG. 14 shows an alternative example of outlet tube 28(4) in which angle d1 at the top of the inlet end 29 is about −2° and angle d2 at the bottom of the inlet end 29 is about 7° which defines an average (center line) of about 2° and a difference (divergence) of about 9°. Angle d3 at the top of the outlet end 31 is about 5° and angle d4 at the bottom of the outlet end 31 is about 13° which defines an average (center line) of about 9° and a difference (divergence) of about 9°. In this example, the minimum slider draft angle for molding may be about 2°.

Figure 16:
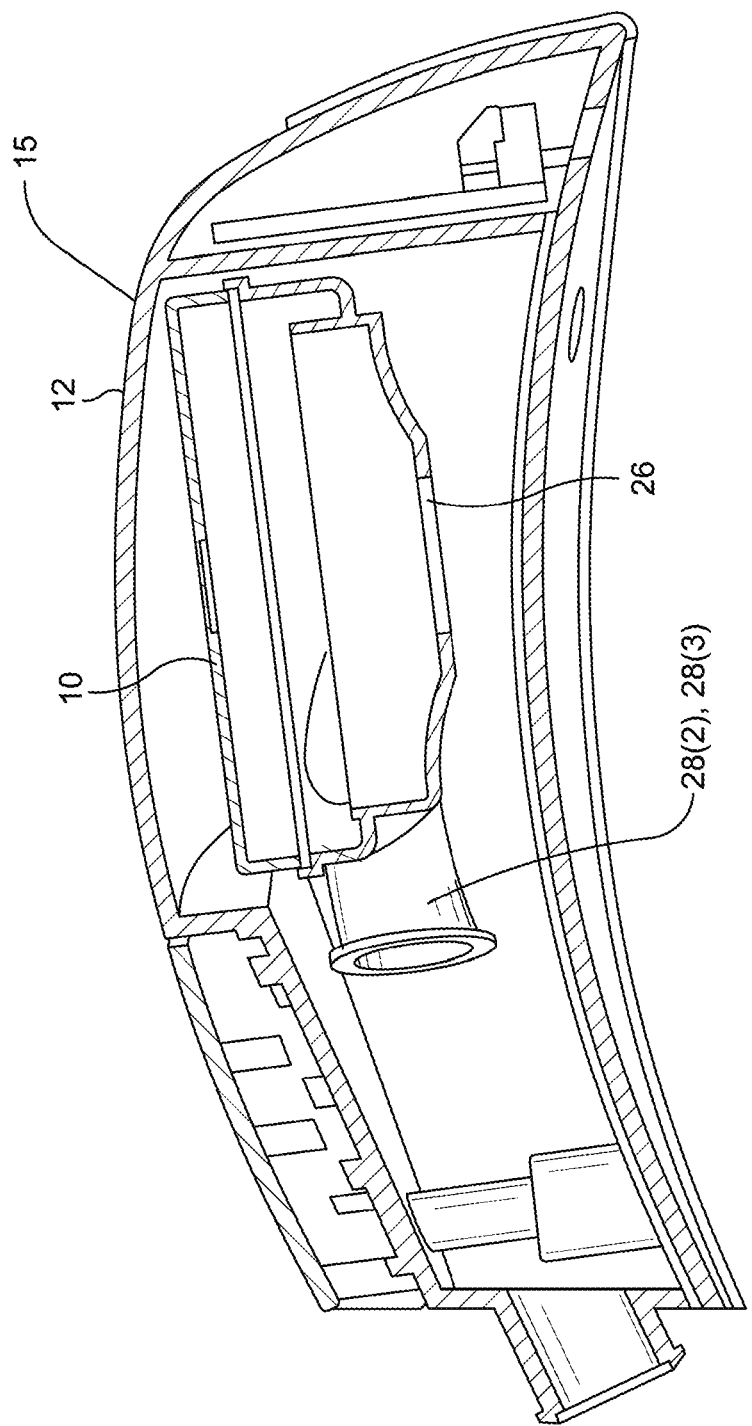
FIG. 16 is a cross-sectional view showing a blower mounted within the casing of a PAP device according to an example of the disclosed technology.

As best shown in FIG. 10, the outlet tube 28(2) and 28(3) is bent or curved with respect to horizontal, i.e., generally upwardly as viewed in FIG. 10. When the blower 10 is mounted within the casing 12 of a PAP device 15 adapted to fit on top of the patient's head in use (e.g., with the inlet 26 oriented downwardly towards the patient's head in use as shown in FIG. 16), the outlet 28(2), 28(3) is oriented such that it is bent or curved downwardly towards the patient's head, so as to better follow the contour of the patient's head in use and direct the outlet flow at a suitable angle in use.

Figure 17:
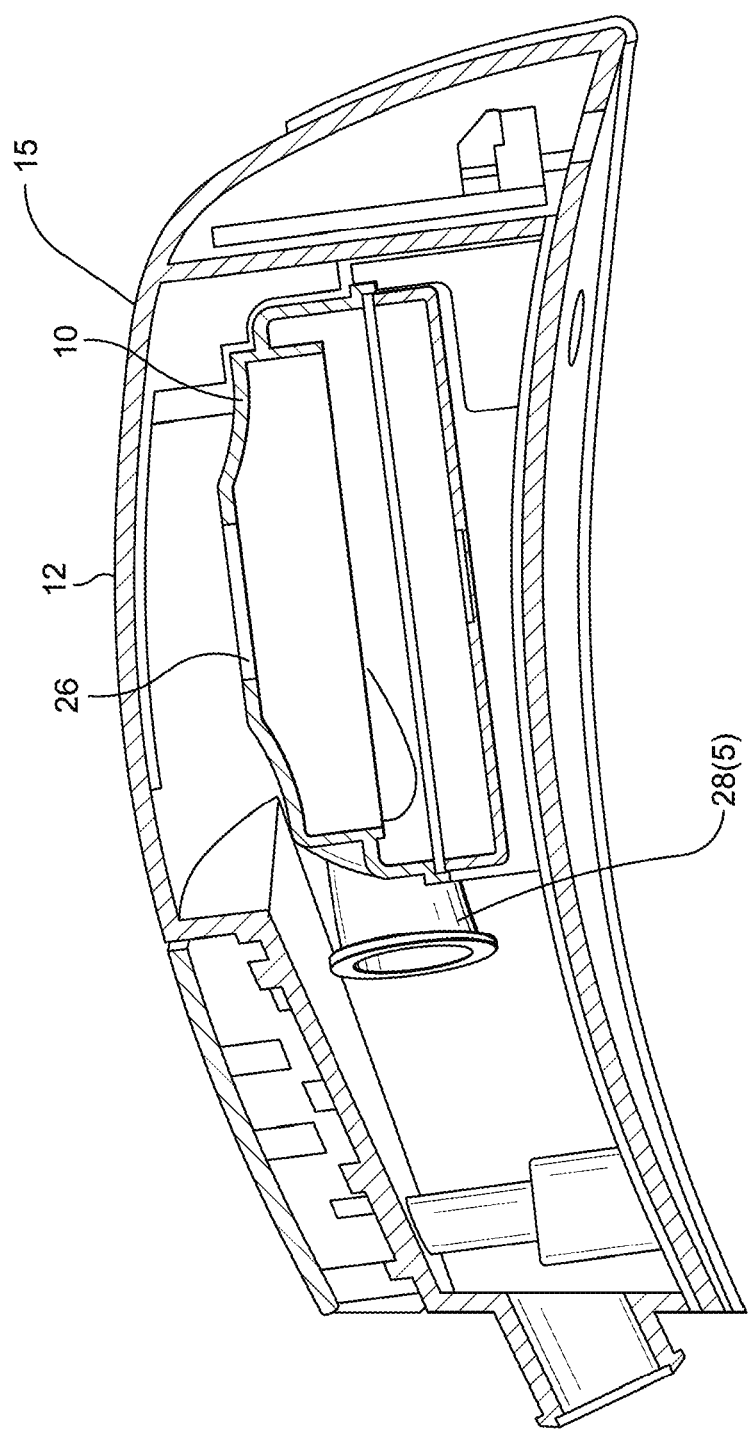
FIG. 17 is a cross-sectional view showing a blower mounted within the casing of a PAP device according to another example of the disclosed technology.
Figure 18:
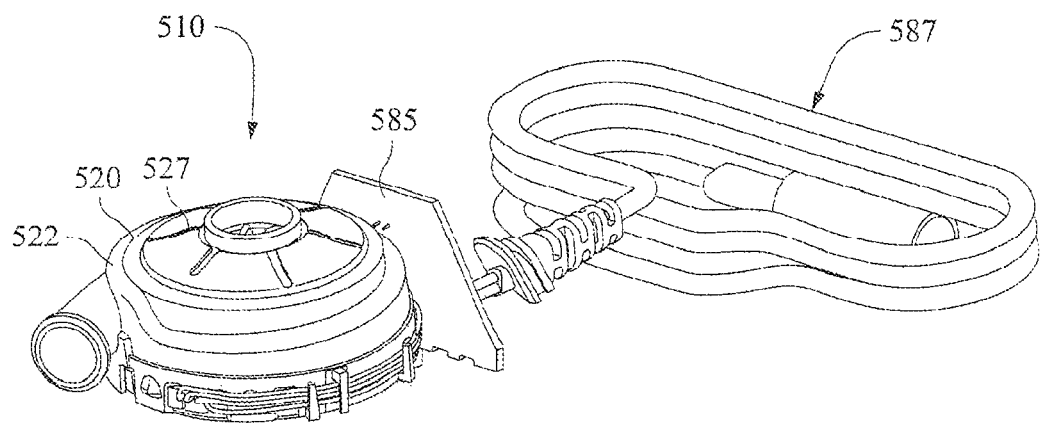
FIG. 18 a top perspective view of a blower according to another example of the disclosed technology.
Figure 19:
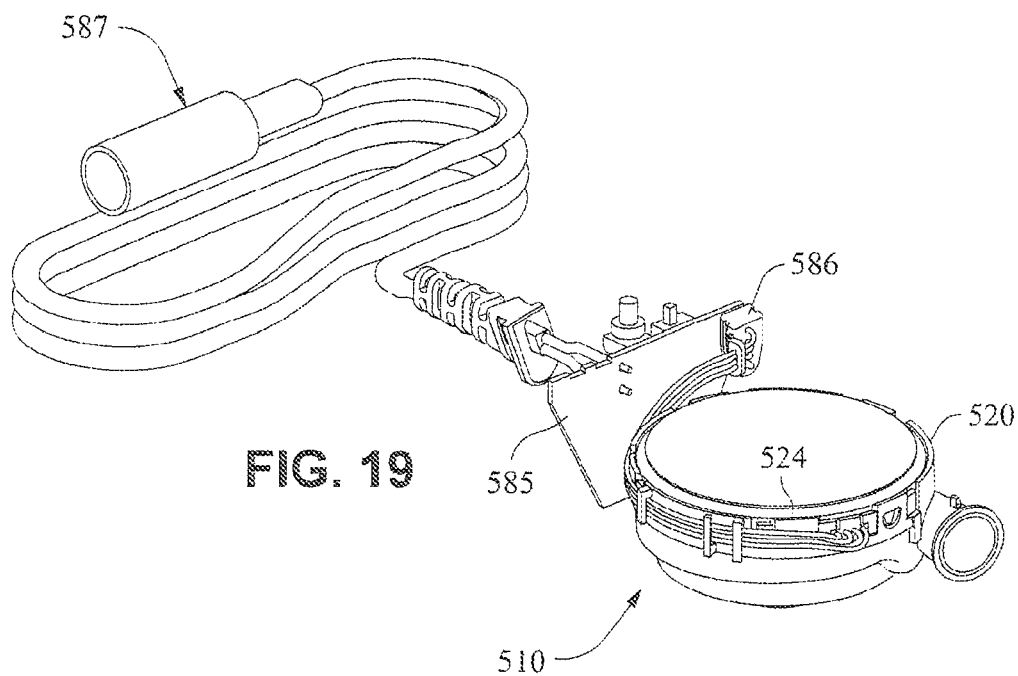
FIG. 19 is a bottom perspective view of the blower of FIG. 18.

In an alternative arrangement, the outlet tube may be bent or curved in the opposite direction to that shown in FIG. 10. This arrangement allows the blower to be mounted within the casing 12 of the PAP device 15 with the inlet 26 oriented upwardly away from the patient's head in use and with the outlet tube 28(5) curved or bent downwardly to follow the contours of the patient's head as shown in FIG. 17.

The blower may be supported within the casing of the PAP device in any suitable manner, e.g., blower supported by a lower wall of the casing, blower suspended from an upper wall of the casing, blower suspension system as described in U.S. application Ser. No. 12/794,206, filed Jun. 4, 2010, which is incorporated herein by reference in its entirety, foam supports, etc.

1.1.2 Connection of Housing Parts

Figure 3:
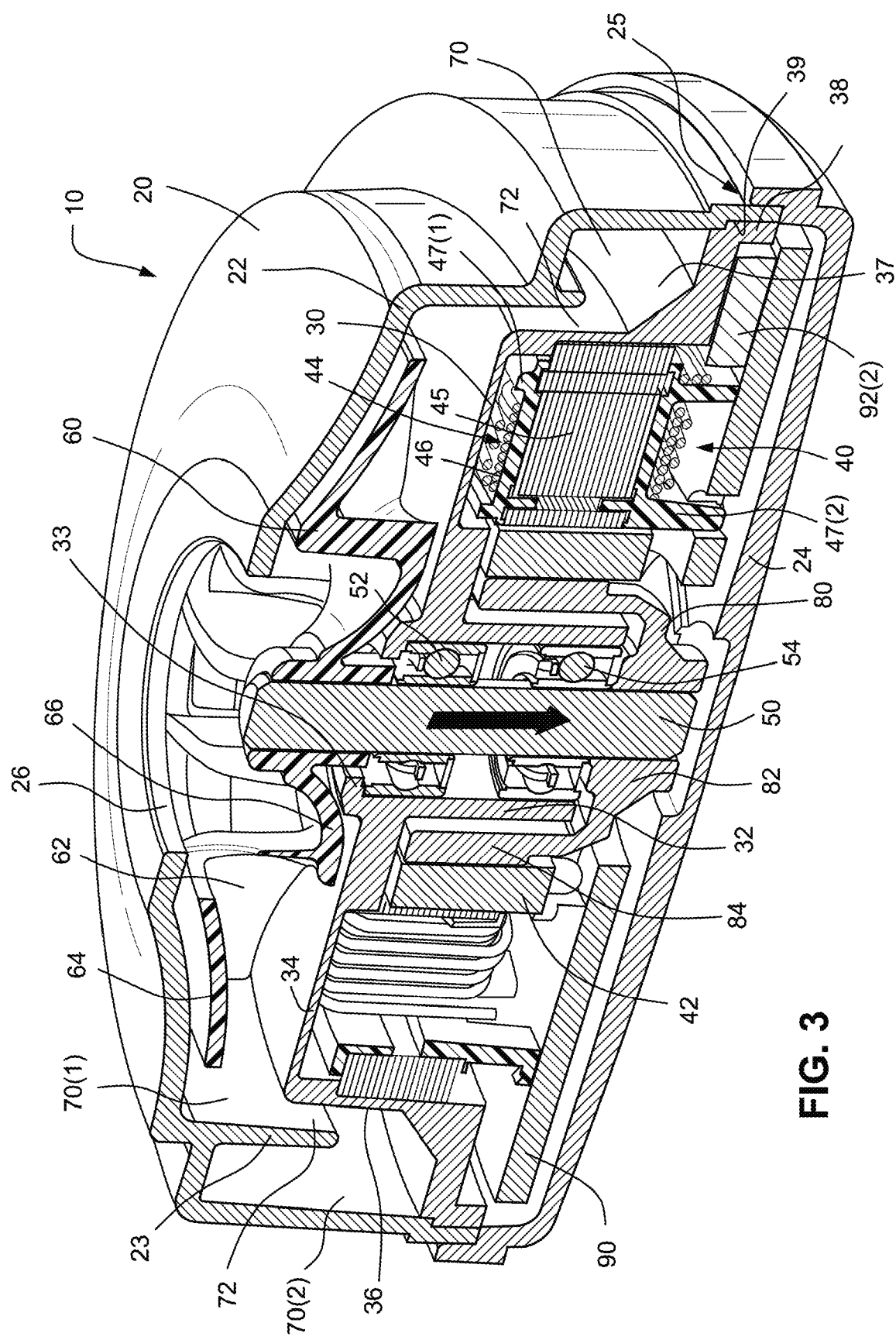
FIG. 3 is a cross-sectional view of the blower of FIG. 1.
Figure 4:
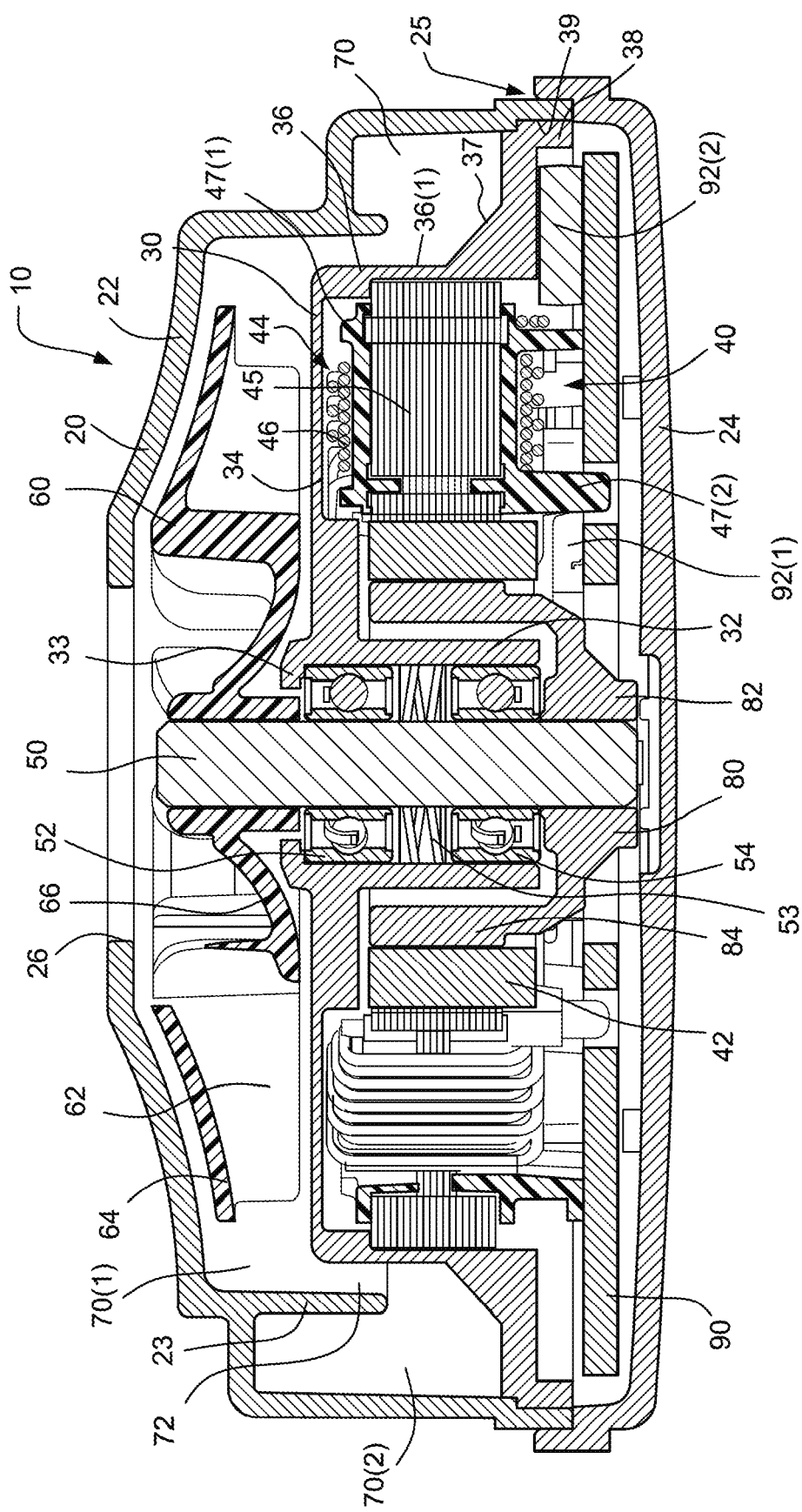
FIG. 4 is another cross-sectional view of the blower of FIG. 1.

As shown in FIGS. 3 and 4, the first and second housing parts 22, 24 may provide a joint 25 (e.g., tongue and groove arrangement or a welded connection) to facilitate alignment and connection.

Alternatively, the first and second housing parts may be connected by a mechanical interlock type arrangement, e.g., snap-fit or snap-lock arrangement. For example, as shown in FIG. 15, the first housing part 22 may include tab members 417 each having an opening 418 adapted to receive or interlock with a corresponding protrusion provided to the second housing part. As illustrated, the opening 418 has an inverted "mickey mouse ear" type shape (i.e., having an arc shape with two opposing semi-circular protrusions at the end opposite the arc), which increases the resiliency of the tab member 417 and prevents accidental breakage. However, it should be appreciated that the opening may have other suitable shapes. The shape is preferably designed to eliminate sharp corners that result in high stress points.

1.1.3 Separating Wall

As best shown in FIGS. 3 and 4, the first housing part 22 cooperates with the stationary component 30 to define a volute 70 that directs air towards the outlet. As illustrated, the first housing part 22 includes a cylindrical, separating wall or baffle 23 that separates the volute 70 into two regions, i.e., a high speed airpath region 70(1) and a low speed airpath region 70(2). In the illustrated example, the low speed airpath region 70(2) is radially offset from the high speed airpath region 70(1). The separating wall 23 extends from a position adjacent the top of the impeller 60 to a position at or beyond the bottom of the impeller 60. The separating wall extends generally parallel to a central axis of the blower, i.e., general vertical orientation as shown in FIG. 4. In use, the separating wall 23 separates the high speed airpath region 70(1) from the low speed airpath region 70(2) so as to minimize air turbulence at relatively high speeds. That is, the separating wall reduces noise and airpath disruption.

At flows other than the ideal design flow, conventional volutes cause asymmetrical flow patterns in and around the impeller. These asymmetrical flow patterns cause pulsating pressure and acoustic noise, as the impeller rotates within the volute. In the example of the present technology, the separating or dividing wall allows asymmetrical flow patterns in the low speed airpath region, while encouraging the high speed airpath region to remain relatively symmetrical in and around the impeller, hence minimizing the pressure pulsations and/or acoustic noise.

Also, the cylindrical configuration of the separating wall or baffle 23 which separates the volute radially provides a relatively small package or compact arrangement (e.g., compared to a volute that may separate the volute axially). This arrangement allows more available motor space.

Also, the first housing part 22 provides a stepped configuration, which adjusts the volume of the volute 70 (i.e., the low speed airpath region 70(2)) around the perimeter of the blower. Specifically, the low speed airpath region includes an expanding volume as it extends towards the outlet, i.e., volute volume larger at the outlet and smaller away from the outlet.

1.2 Stationary Component

As described in greater detail below, the stationary component mechanically supports the whole motor and driver assemblies as well as provides one or more additional functions such as (i) shielding to prevent blade pass tone, (ii) bearing tube for bearing retainment and alignment, (iii) assists in defining the volute, (iv) correct alignment and positioning of the stator assembly, (v) protects or separates the motor from the airpath, and/or (vi) central aperture for the shaft or rotor 50.

As shown in FIGS. 3 and 4, the stationary component 30 includes a tube portion or bearing tube portion 32, a shield portion 34 provided to one end of the tube portion, and a downwardly and outwardly extending end portion 36 extending from the shield. In the illustrated example, the stationary component is integrally molded as a one-piece structure. However, the stationary component may be constructed in other suitable manners.

The interior surface of the tube portion 32 is structured to retain and align the bearings 52, 54 that rotatably support the shaft 50. In the illustrated example, the tube portion 32 is structured such that upper and lower ends of the tube portion are adapted to support bearings of the same size. However, a tube portion structured to support mixed bearing sizes may be used. As illustrated, the upper end of the tube portion includes a flange 33 that provides a stop for the bearing 52 at the upper end. The flange 33 also defines a central aperture 35 for the shaft or rotor 50 to pass through for engagement with the impeller 60. A hub 82 for the magnet support 80 provides a stop for the bearing 54 at the lower end of the tube portion. Further examples of tube portions are disclosed in U.S. application Ser. No. 12/312,042, filed Apr. 23, 2009, and Ser. No. 12/155,528, filed Jun. 5, 2008, each of which is incorporated herein by reference in its entirety. For assembly, the ball bearings are inserted in the bearing housings 52, 54 and pushed in and over a projection within the bearing housings to lock the ball bearings within the bearing housings. A spring 53 is positioned between the two bearings 52, 54 to maintain the bearings in the correct alignment.

The outer edge of the shield portion 34 substantially aligns with or extends radially beyond the outer edge of the impeller 60. The edge of the shield portion 34 cooperates with the separating wall 23 to define a narrow gap 72 between the high speed airpath region 70(1) and the low speed airpath region 70(2). However, in an alternative example, the outer edge of the shield portion 34 may not extend as far as the outer edge of the impeller 60. The shield portion 34 assists in preventing blade pass tonal noise when the impeller is rotating as it provides a barrier between spinning impeller blades and the fixed stator end portion 36.

The end portion 36 cooperates with the first housing part 22 to define the volute 70. The inner edge of the end portion may include an angled surface 37. Alternatively, such surface 37 may include a curved profile. As illustrated, the free end of the end portion includes a tab 38 adapted to engage within a respective slot 39 provided in the first housing part 22 to align and retain the stationary component within the housing. Also, the downward section 36(1) of the end portion is adapted to engage the stator assembly of the motor 40 as described below. A seal may be provided between the tab 38 and the slot 39 to facilitate a seal for the volute. The seal also provides a spring force to keep the tab and slot engaged.

Figure 8:
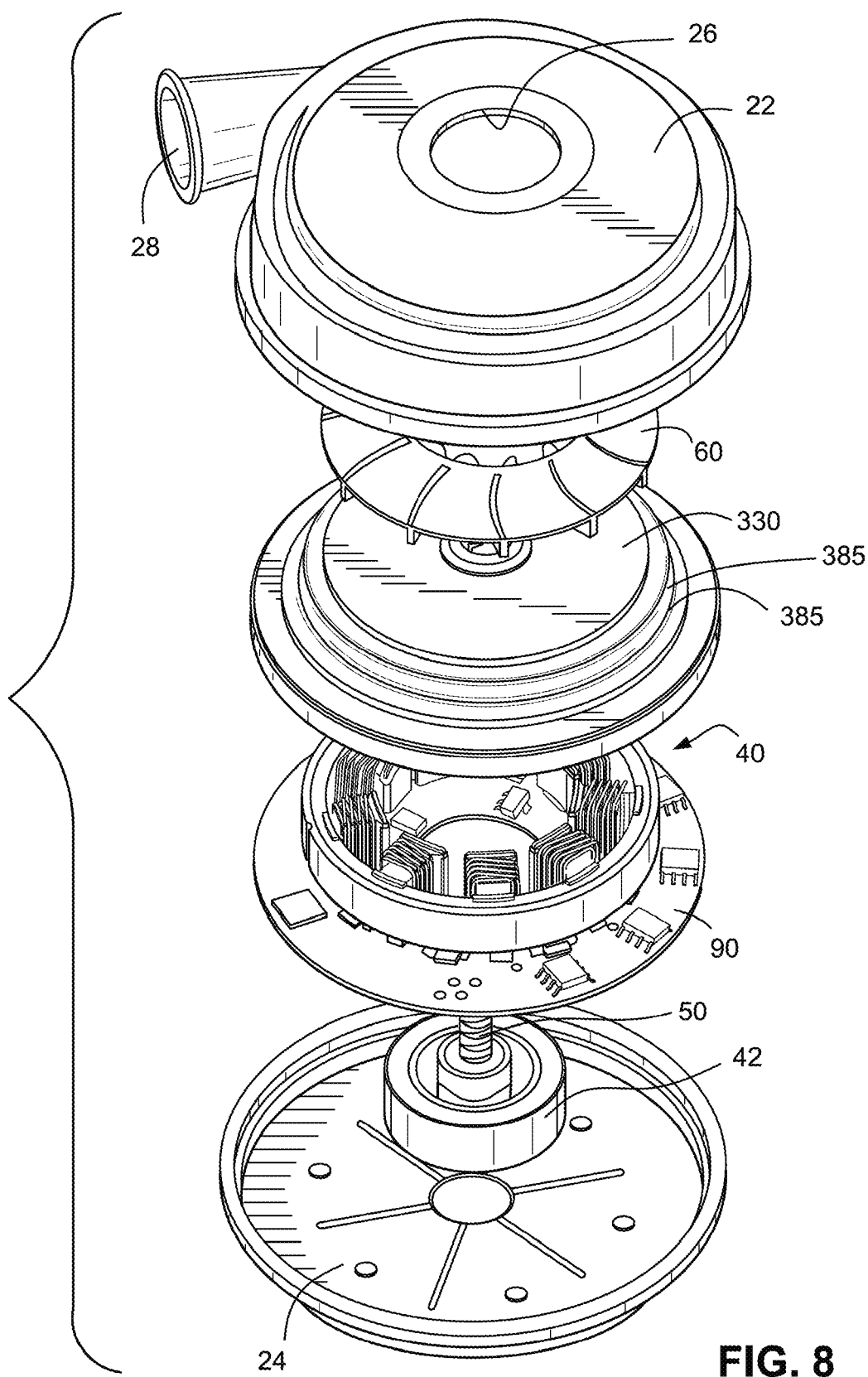
FIG. 8 is an exploded view of a blower according to another example of the disclosed technology.
Figure 9:
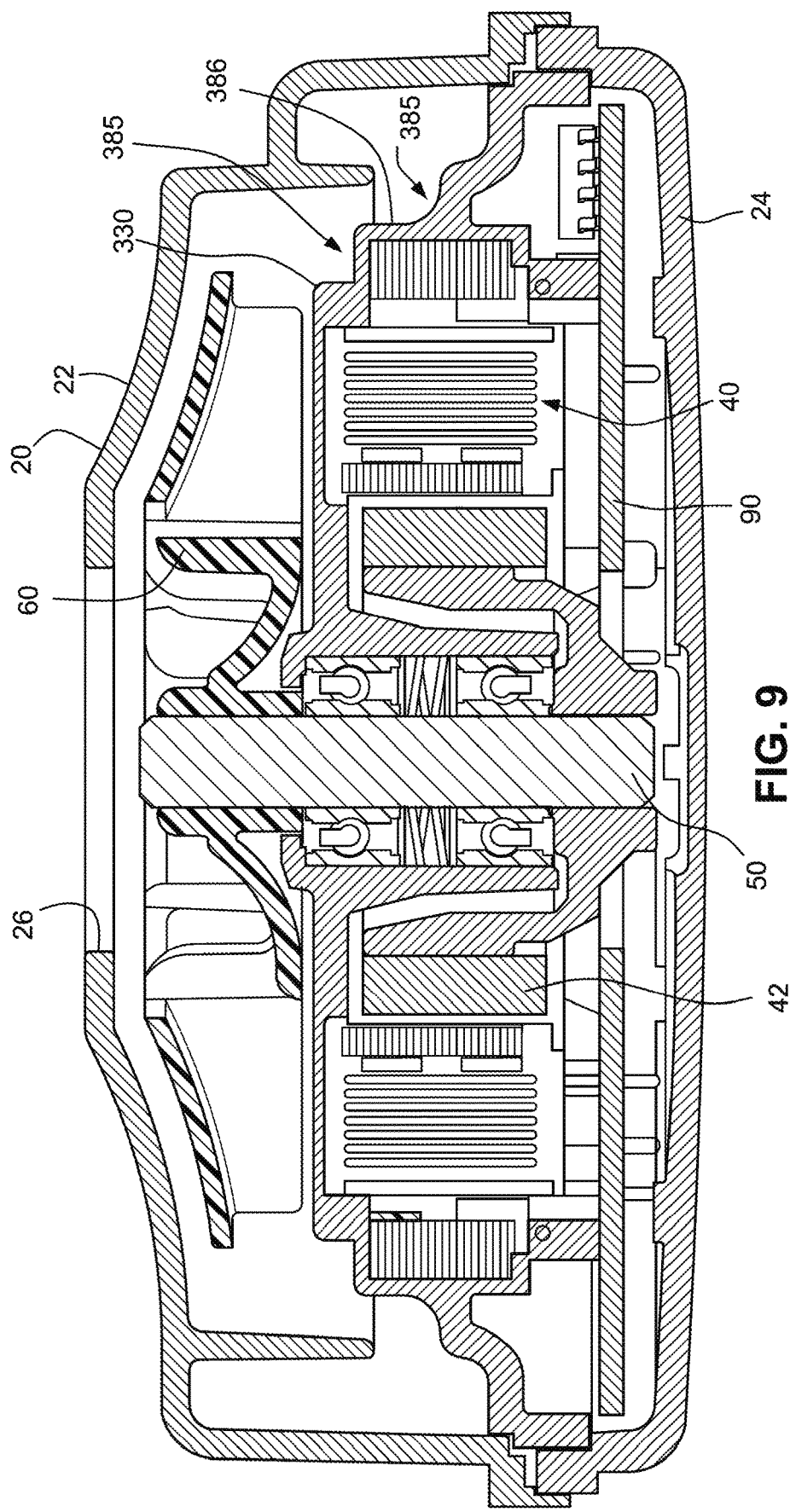
FIG. 9 is a cross-sectional view of the blower of FIG. 8.

FIGS. 8 and 9 illustrate a blower including a stationary component according to an alternative example. The remaining components of the blower are substantially similar to that described above and indicated with similar reference numerals. In this example, the downwardly and outwardly extending end portion 336 of the stationary component 330 includes multiple steps 385, e.g., two steps. However, any suitable number of steps may be provided, e.g., 1, 2, 3, or more steps. The inner edge of each step may include a curved profile.

1.3 Motor

The motor 40 includes a magnet 42, a shaft 50 and a stator assembly 44 including windings that generate the electromagnetic field to cause spinning movement of the shaft 50 via the magnet 42. The magnet 42 is coupled to the shaft 50 by a magnet support 80 which includes a hub 82 engaged with the shaft 50 and an arm 84 to support the magnet 42. The arm 84 of the magnet support 80 extends radially outwards and then vertically upwards to surround the bearing tube portion 32 of the stationary component 30. The arm 84 of the magnet support 80 facilitates alignment of the magnet 42 with the stator assembly 44. The magnet support 80 is rotated to enable rotation of the shaft 50 and the impeller 60 attached the shaft due to the interaction of the magnet 42 and the stator assembly 44. This arrangement provides an internal rotor with a cup-like configuration. As shown in FIG. 3, the shaft 50 may be magnetically biased downwardly toward the second housing part 24 (as indicated by the arrow). However, an axial force may be provided by a bearing preload, e.g., a spring 53 between outer races of the bearings 52, 54 as shown in FIG. 4.

The stator assembly 44 includes a stator core or electromagnetic core 45 (e.g., including a plurality of laminations stacked on top of one another) on which stator coils or windings 46 are wound. First and second insulators 47(1), 47(2) (also referred to as slot insulators or slot liners) are provided on opposing sides of the stator core 45 to insulate the stator core 45 from the stator coils 46. Further details of such insulators are disclosed in U.S. application Ser. No. 12/310,437, filed Feb. 25, 2009, which is incorporated herein by reference in its entirety.

As illustrated, the exterior surface of the stator assembly 44 (i.e., exterior surface of the stator core 45) may be supported and retained by the stationary component 30 (i.e., the downward section 36(1) of the end portion 36). The stationary component provides correct alignment and positioning of the stator assembly. Also, the downward section 36(1) engaging the stator core 45 is exposed to the flow of gas, which allows forced-convection cooling of the stator core as gas flows through the housing in use. In addition, this arrangement may assist in heating the gas or patient air.

1.3.1 Motor Control

A printed circuit board assembly (PCBA) 90 is mounted to the lower surface of the housing 20. In an example, the PCBA is a pulse-width modulation (PWM) controller to control the motor. The PCBA 90 may contain one or more sensors or control chips 92(1), 92(2) to assist in controlling the spinning movement of the shaft and hence the load, e.g., impeller. For example, the PCBA may include a Hall sensor to sense the position of shaft or a thermal sensor. Alternatively, the blower may use a sensorless, brushless DC motor control.

In an example, the PCBA is provided within the blower to commutate the motor, control the motor speed to be constant (even with varying flow load as the patient breathes), and/or provide over-temperature and over-speed safety cut-outs. The PCBA includes a motor commutation circuit. With the application of power and an input command, this circuit causes the rotor to turn. This circuitry may be integral or remote from the motor.

The blower can be completely driven by hardware and not software reliant. The speeds may be set manually by the patient. In an example, the blower may be adapted to produce a maximum pressure of 15 $cmH_2O$ or preferably 12 $cmH_2O$ at 6000 feet (i.e., 6000 feet being standard cabin pressure for jet aircraft). However, other pressures such as 8 $cmH_2O$ or 10 $cmH_2O$ or less are also within the scope of the technology. The light and compact arrangement of the blower is adapted for travel and able to operate up to 6000 ft.

The blower may be powered by batteries, or a switch mode power supply. Where batteries are used, there is a tendency for the voltage to reduce as the battery is discharged. If the blower is driven with fixed PWM, this would result in a reduction of speed and hence pressure as the battery discharges. Alternatively, speed control can be used to keep the pressure relatively constant as the battery discharges.

1.4 Impeller

In the illustrated example, the impeller 60 includes a plurality of continuously curved or straight blades 62 sandwiched between a pair of disk-like shrouds 64, 66. The lower shroud 66 incorporates the hub or bushing that is adapted to receive the shaft 50. Also, the impeller includes a tapered configuration wherein the blades taper towards the outer edge. Further details of impellers are disclosed in WO 2007/048206 A1, which is incorporated herein by reference in its entirety.

1.5 Fluid Flow Path

Air enters the blower 10 at the inlet 26 and passes into the impeller 60 where it is accelerated tangentially and directed radially outward. Air then flows into the high speed airpath region 70(1) of the volute 70, and then through the gap 72 into the low speed airpath region 70(2) of the volute 70. Air is directed along the volute towards the tangential outlet 28, which volute has an increasing volume.

1.6 Exemplary Applications

The blower provides a relatively flat, compact, and lightweight arrangement. For example, the blower may weight less than 150 grams, e.g., 110 grams. In an example, the blower may be structured to provide pressurized air in the range of 2-30 cmH$_2$O, such as 2-15 cmH$_2$O, e.g., up to 12 cmH$_2$O at 24000 rpm.

The blower may be used for CPAP and/or ventilator applications. In an example, the blower may be incorporated into the patient interface, headgear, or carried by the patient, examples of which are disclosed in U.S. Provisional Application No. 61/272,188, filed Aug. 28, 2009, incorporated herein by reference in its entirety.

Figure 6:
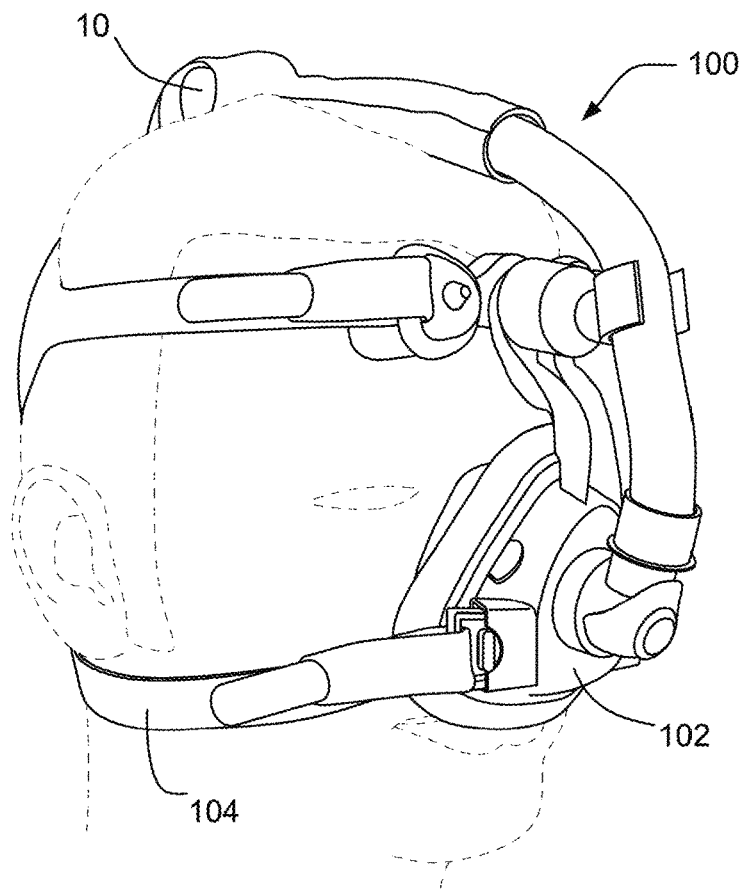
FIG. 6 is a perspective view of a PAP system including the blower of FIG. 1.

For example, FIG. 6 illustrates a PAP system 100 including a patient interface including a sealing arrangement 102 adapted to form a seal with the patient's nose and/or mouth and headgear 104 to support the sealing arrangement in position on the patient's head. As illustrated, the blower 10 may be supported by the patient interface on the patient's head and in communication with the patient interface.

Figure 7:
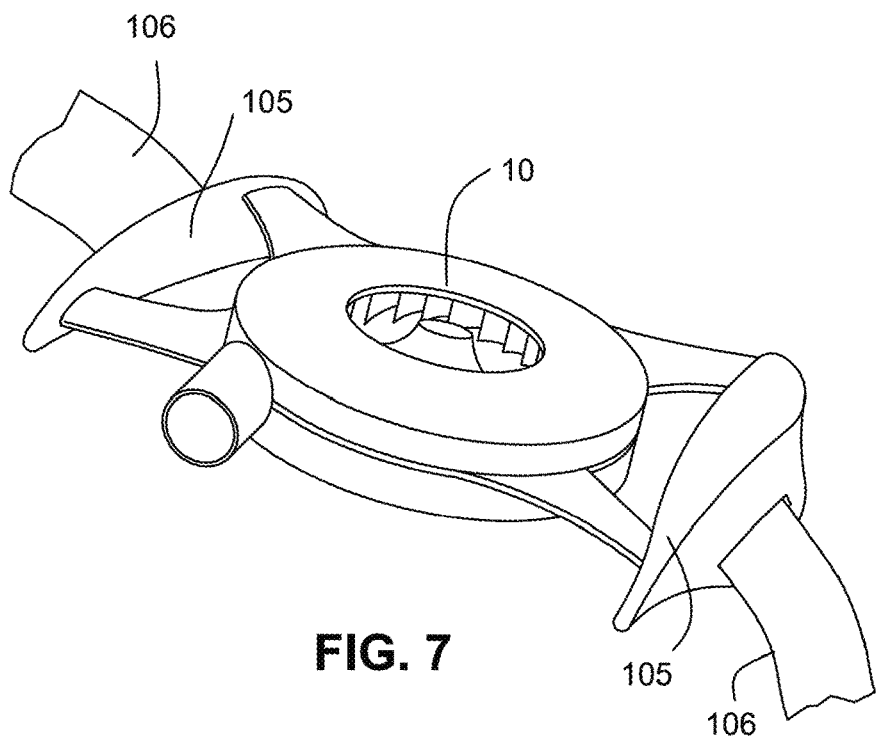
FIG. 7 is a perspective view of the blower of FIG. 1 including headgear connectors according to an example of the disclosed technology.

FIG. 7 illustrates an alternative arrangement in which headgear connectors 105 are provided to respective sides of the blower 10. The headgear connectors 105 are adapted to attach to respective headgear straps 106 for supporting the blower on top of the patient's head in use.

1.6.1 Alternative CPAP Application

FIGS. 18-52 illustrate another example of a blower 510 for an integrated CPAP system incorporating a patient interface and a head/body worn PAP device or flow generator (e.g., see FIGS. 49-52 described below). In an example, the blower may be structured to provide pressurized air in the range of 2-30 cmH$_2$O, e.g., 2-15 cmH$_2$O, such as 8 cmH$_2$O, 10 cmH$_2$O and/or 12 cmH$_2$O. In an example, the blower may provide fixed pressure settings (e.g., 8 cmH$_2$O, 10 cmH$_2$O and/or 12 cmH$_2$O) adjustable by the user. The blower may be powered by a power cord assembly or by a battery (e.g., charger pack for battery provided as accessory).

As best shown in FIGS. 18-21, the blower 510 includes a housing 520 with first and second housing parts 522, 524, a stationary component 530 overmolded with a stator assembly 544, magnet 542 coupled to the shaft 550 by magnet support 580, impeller 560 coupled to an end portion of the shaft 550, and PCBA 590 for motor control.

Chimney Provided to First Housing Part

In an example, as best shown in FIGS. 18, 20, 21, and 22, a chimney or inlet tube portion 527 is provided to the inlet 526 of the first housing part 522. The chimney 527 (e.g., constructed of TPU alloy, e.g., TPE, or other suitable material) may be overmolded to the first housing part 522. However, the chimney may be coupled to the first housing part 522 in other suitable manners, e.g., mechanical interlock.

The chimney 527 includes a base 527(1) that extends along the upper wall of the first housing part 522 and a tube portion 527(2) aligned with the inlet 526. Such chimney may help to dampen vibrations when the blower is mounted within the casing of the PAP device.

Shield Provided to Second Housing Part

Figure 20:
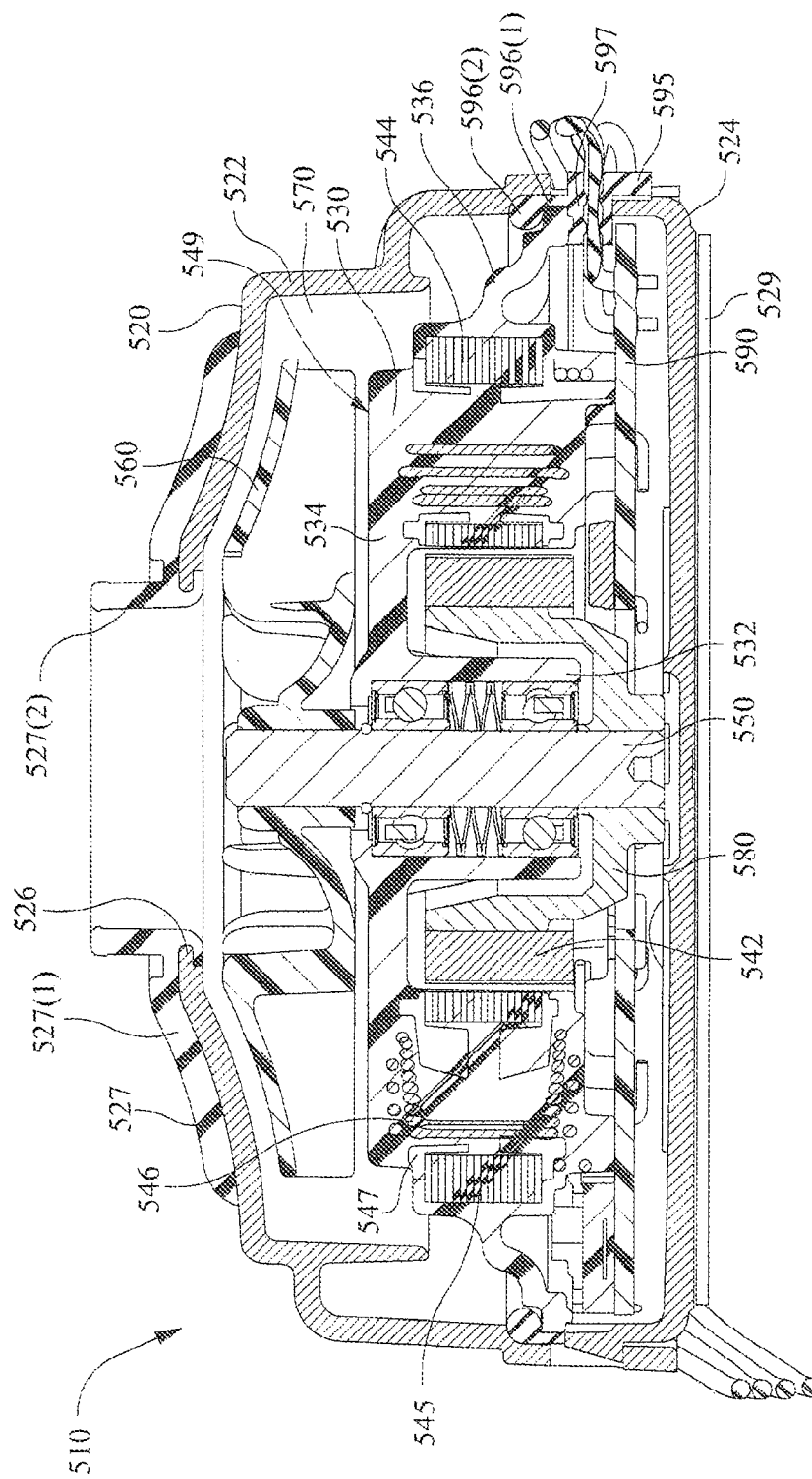
FIG. 20 is a cross-sectional view of the blower of FIG. 18.
Figure 23:
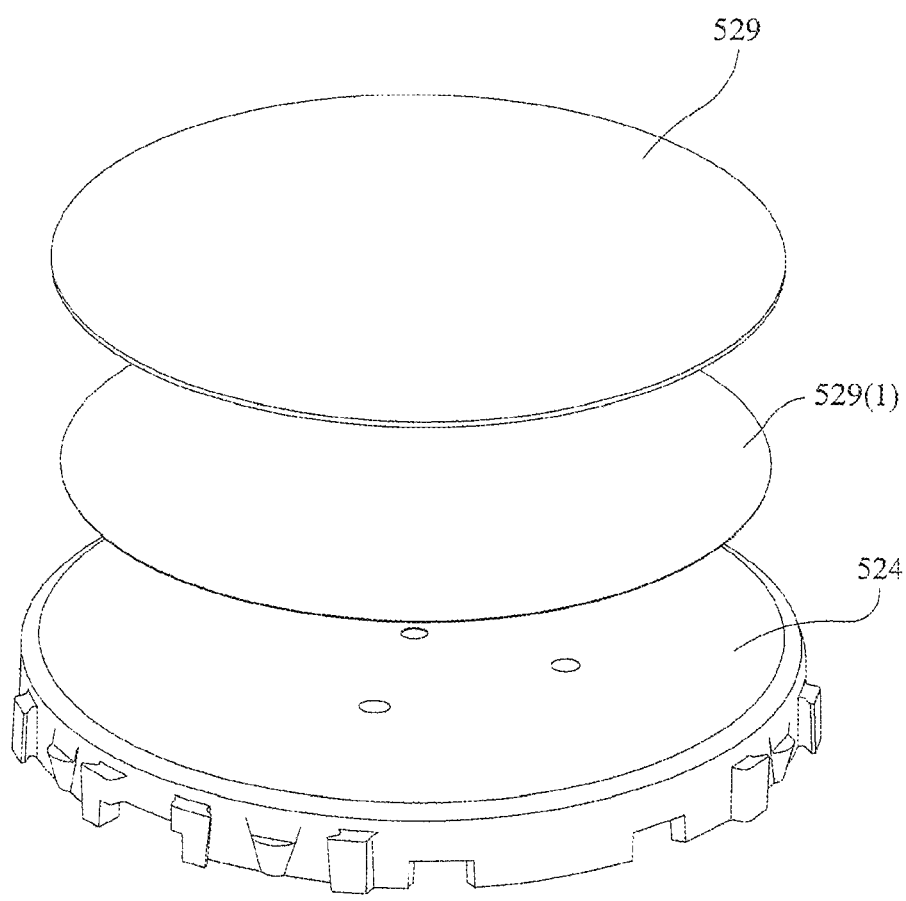
FIG. 23 is an exploded view of the second housing part and shield of the blower of FIG. 18.

In an example, as best shown in FIGS. 20 and 23, a shield or plate 529 is provided to the second housing part 524. The shield 529 may be adhered to the bottom wall of the second housing part 524, e.g., by an adhesive disk 529(1) as shown in FIG. 23. However, the shield may be coupled to the second housing part 524 in other suitable manners.

As shown in FIG. 20, the shield 529 (e.g., constructed of stainless steel) is positioned along the second housing part 524 which is adjacent the PCBA 590 to prevent electromagnetic interference (EMI) of the PCBA 590.

Stationary Component Overmolded with Stator Assembly

In an example, the stationary component 530 (e.g., constructed of liquid crystal polymer (LCP)) may be integrated with a stator assembly 544 (e.g., including insulators constructed of liquid crystal polymer (LCP)), e.g., by overmolding, to form a one-piece overmolded stationary assembly 549. Such overmolded assembly may provide better shock and vibration performance, more compact (e.g., less axial height), better strength and tolerance of harsh environments, and/or lower cost.

Figure 24:
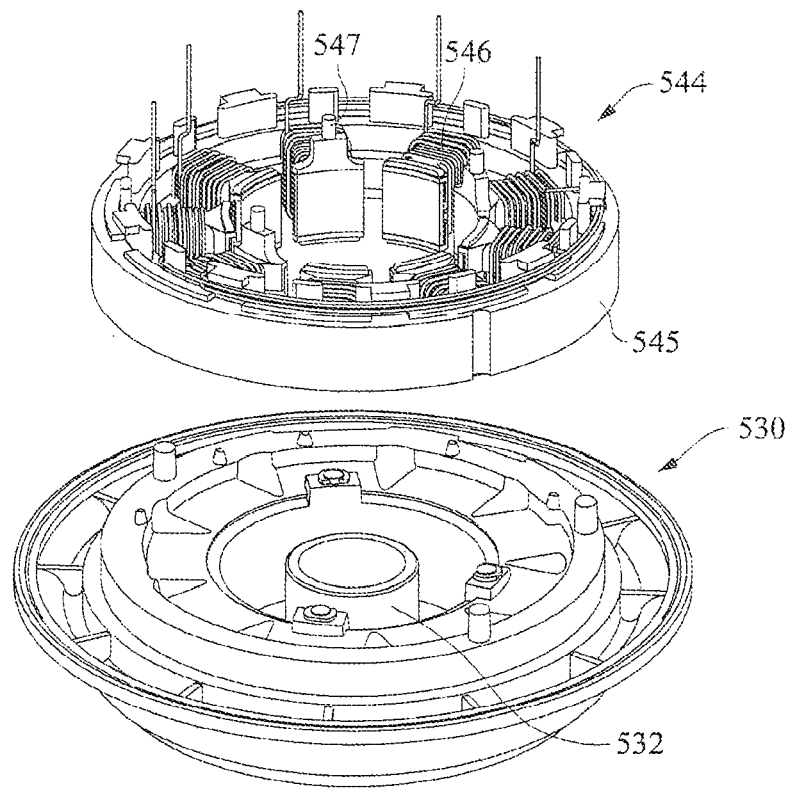
FIG. 24 is an exploded view of a stator assembly and stationary component of the blower of FIG. 18.
Figure 25:
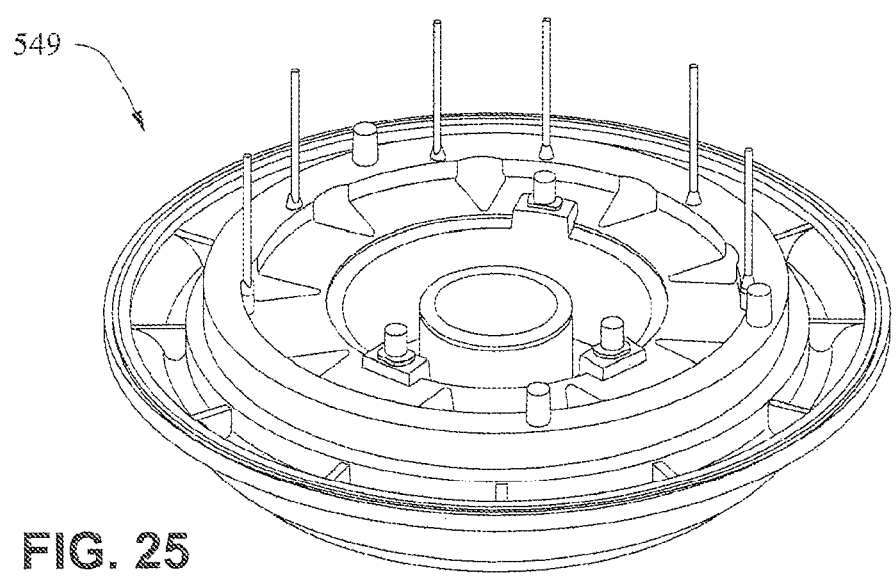
FIG. 25 is a perspective view of the overmolded stationary component and stator component of the blower of FIG. 18.
Figure 29:
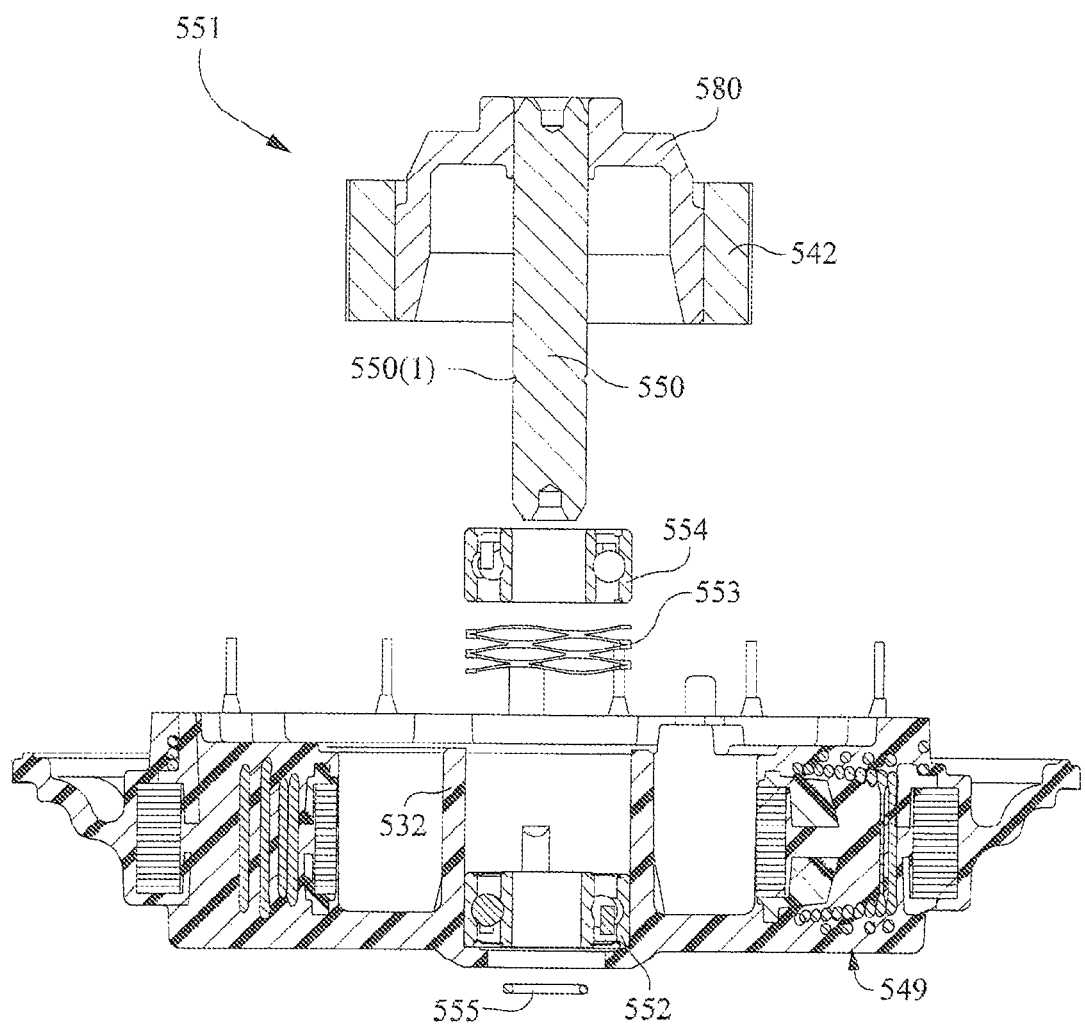
FIG. 29 is an exploded view of the overmolded stationary component and stator assembly along with bearings, shaft, magnet support, and magnet of the blower of FIG. 18.

FIG. 24 shows an example of the stator assembly 544 (including a core 545, windings 546, and insulators 547 (e.g., see FIG. 20) as described above) and a stationary component 530 (including a bearing tube portion 532, shield portion 534, and downwardly and outwardly extending end portion 536 (e.g., see FIG. 20) as described above). The stationary component 530 is shown in the opposite orientation to that shown in FIGS. 20 and 21, i.e., the end closest to the second housing part 524 facing upwards. Thus, the stator assembly is inserted into the stationary component from the bottom or lower end. FIG. 25 shows the stationary component 530 and stator assembly 544 overmolded with one another to establish the one-piece overmolded stationary assembly 549. FIGS. 20 and 29 are exemplary cross-sectional views of the one-piece overmolded stationary assembly 549.

Rotor Install to Overmolded Stationary Assembly

Figure 26:
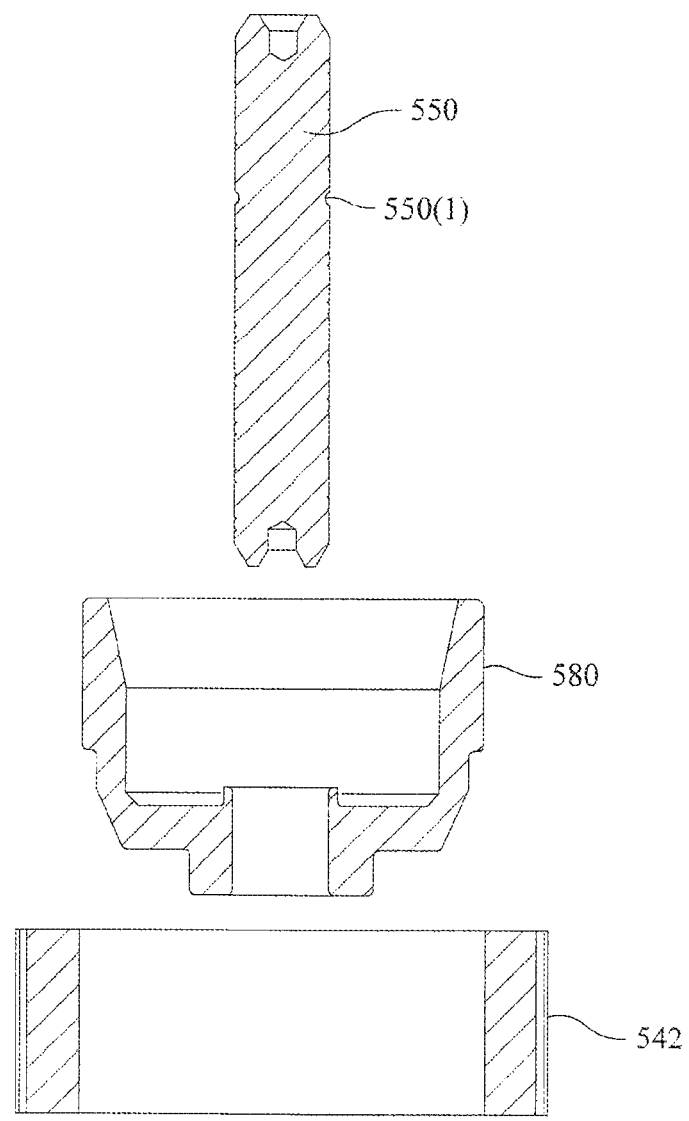
FIG. 26 is an exploded view of the shaft, magnet support, and magnet of the blower of FIG. 18.
Figure 27:
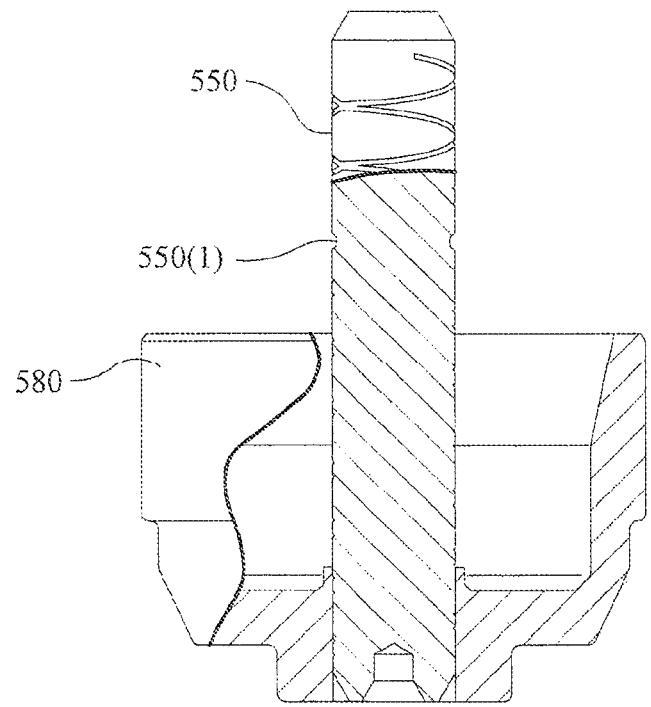
FIG. 27 is a cross-sectional view of the shaft and magnet support of the blower of FIG. 18.
Figure 28:
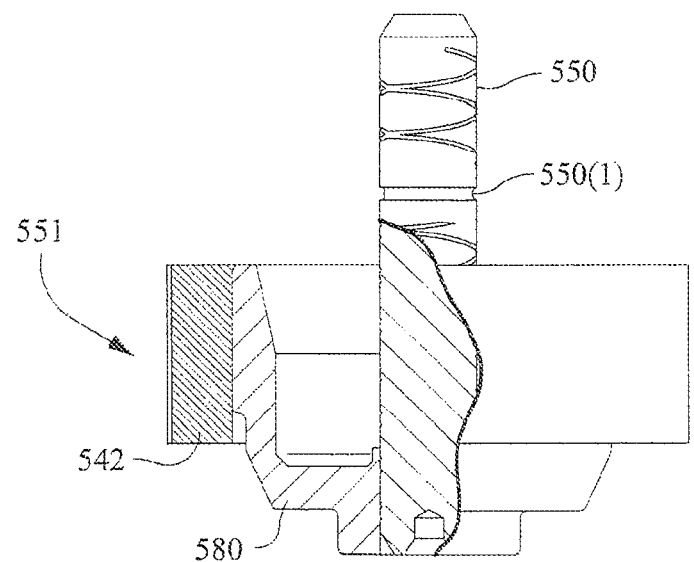
FIG. 28 is a cross-sectional view of the shaft, magnet support, and magnet of the blower of FIG. 18.

FIGS. 26 to 28 show various views of the shaft 550 (e.g., constructed of stainless steel), magnet support 580 (e.g., constructed of stainless steel), and magnet 542 as described above. Such assembled components establish a shaft assembly or rotor assembly 551 which is assembled to the overmolded stationary assembly 549.

Figure 30:
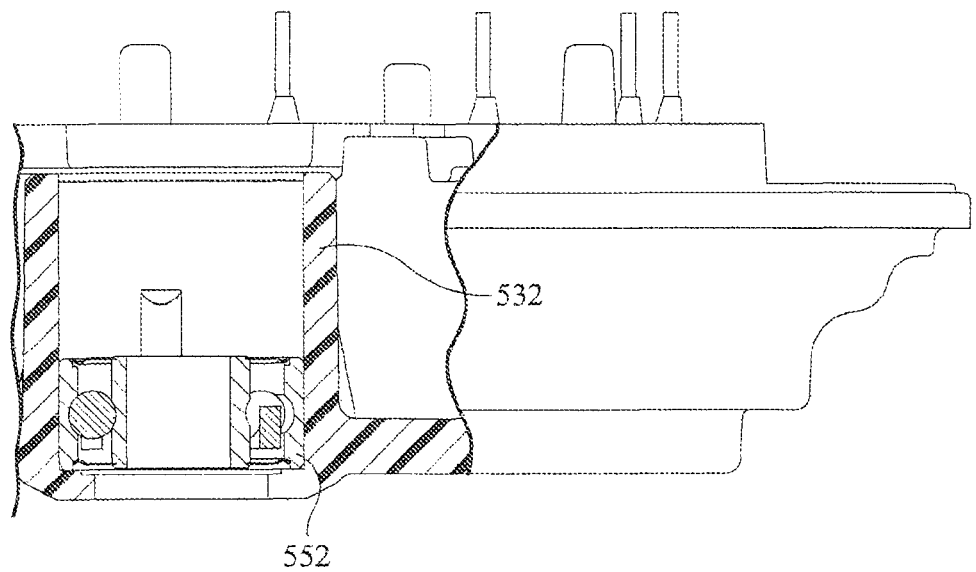
FIG. 30 is a cross-sectional view of the overmolded stationary component and stator assembly along with a bearing of the blower of FIG. 18.
Figure 31:
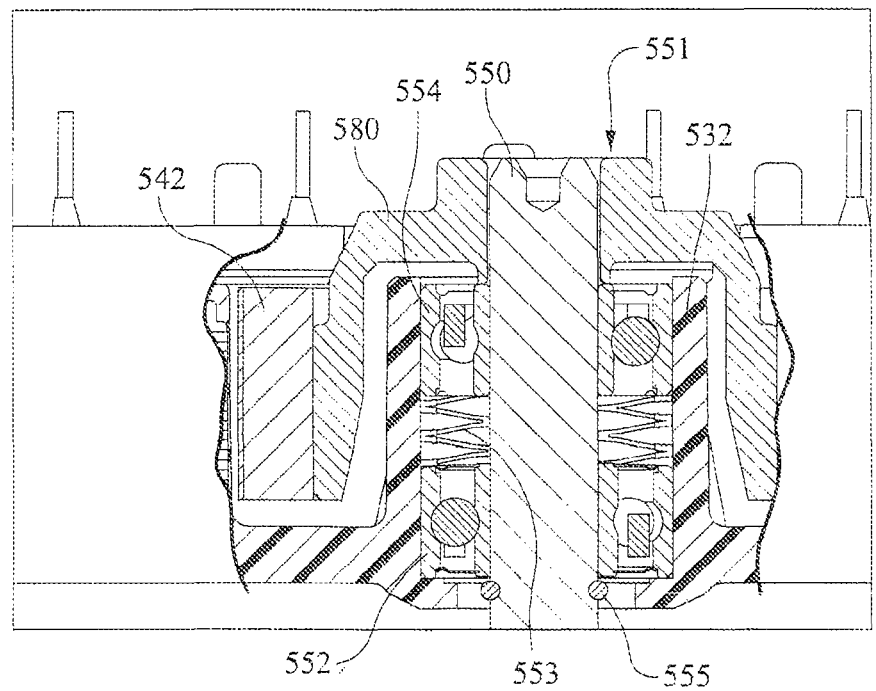
FIG. 31 is a cross-sectional view showing assembly of the components of FIG. 29.
Figure 32:
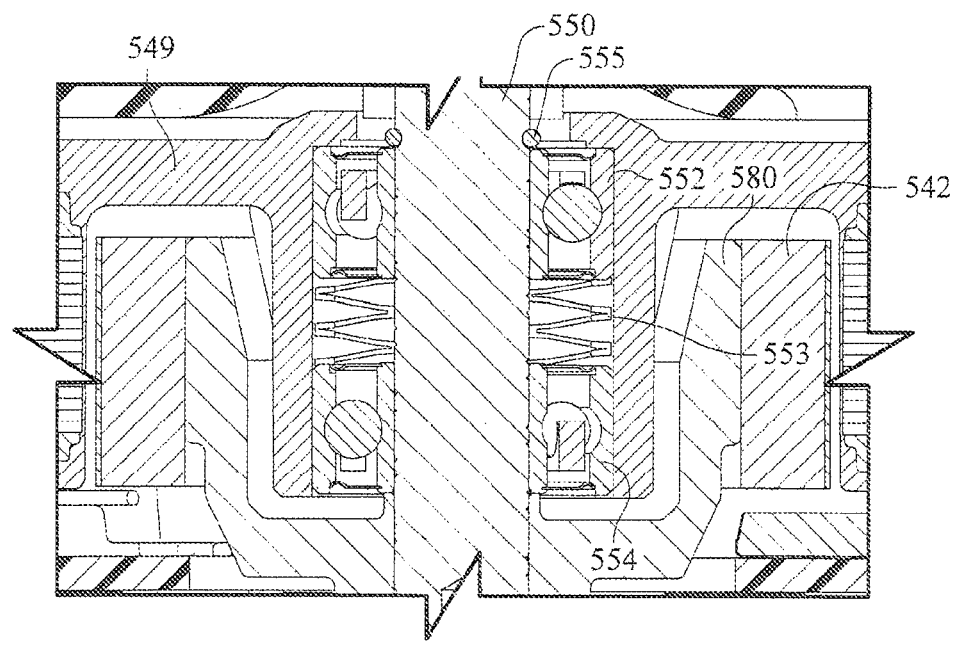
FIG. 32 is another cross-sectional view showing assembly of the components of FIG. 29.

FIGS. 29-32 show various views of the assembly of the shaft assembly 551 to the overmolded stationary assembly 549. As illustrated, the interior surface of the tube portion 532 is structured to retain and align the bearings 552, 554 that rotatably support the shaft 550. A spring 553 (e.g., crest to crest or wave spring constructed of stainless steel) is positioned between the two bearings 552, 554 to maintain the bearings in the correct alignment. In an example, as shown in FIGS. 29 and 30, the bearing 552 positioned closest to the impeller may be initially press-fit into the tube portion 532 (i.e., press-fit outer race of the bearing to the tube portion) before installing the other bearing, spring, and shaft assembly.

Also, a retaining ring 555 (e.g., snap ring constructed of beryllium copper (BeCu) or other suitable material) is provided to the shaft 550 to retain the shaft assembly 551 to the overmolded stationary assembly 549. As best shown in FIGS. 26-29, the shaft 550 includes a groove 550(1) to engage the ring 555.

Figure 21:
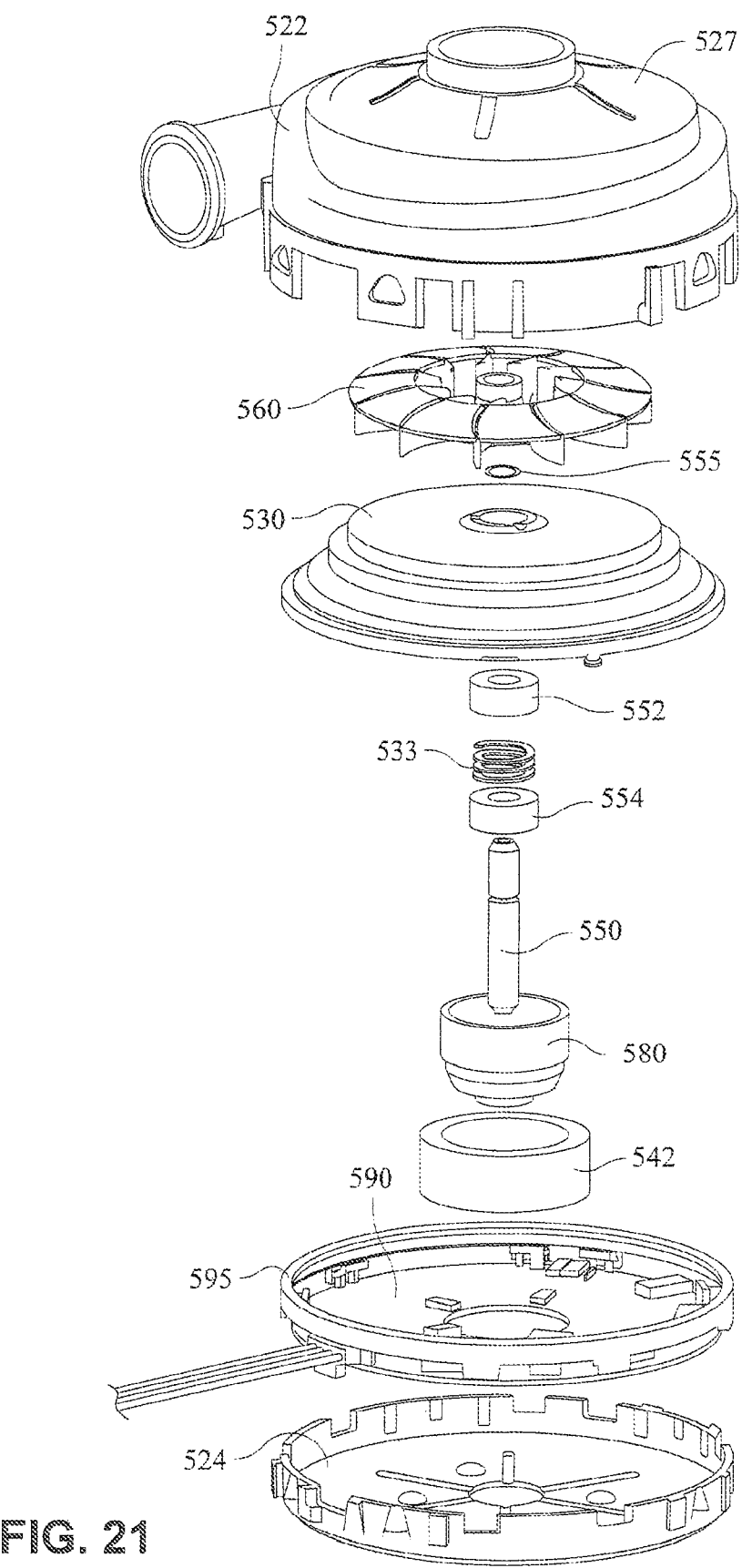
FIG. 21 is an exploded view of the blower of FIG. 18.
Figure 22:
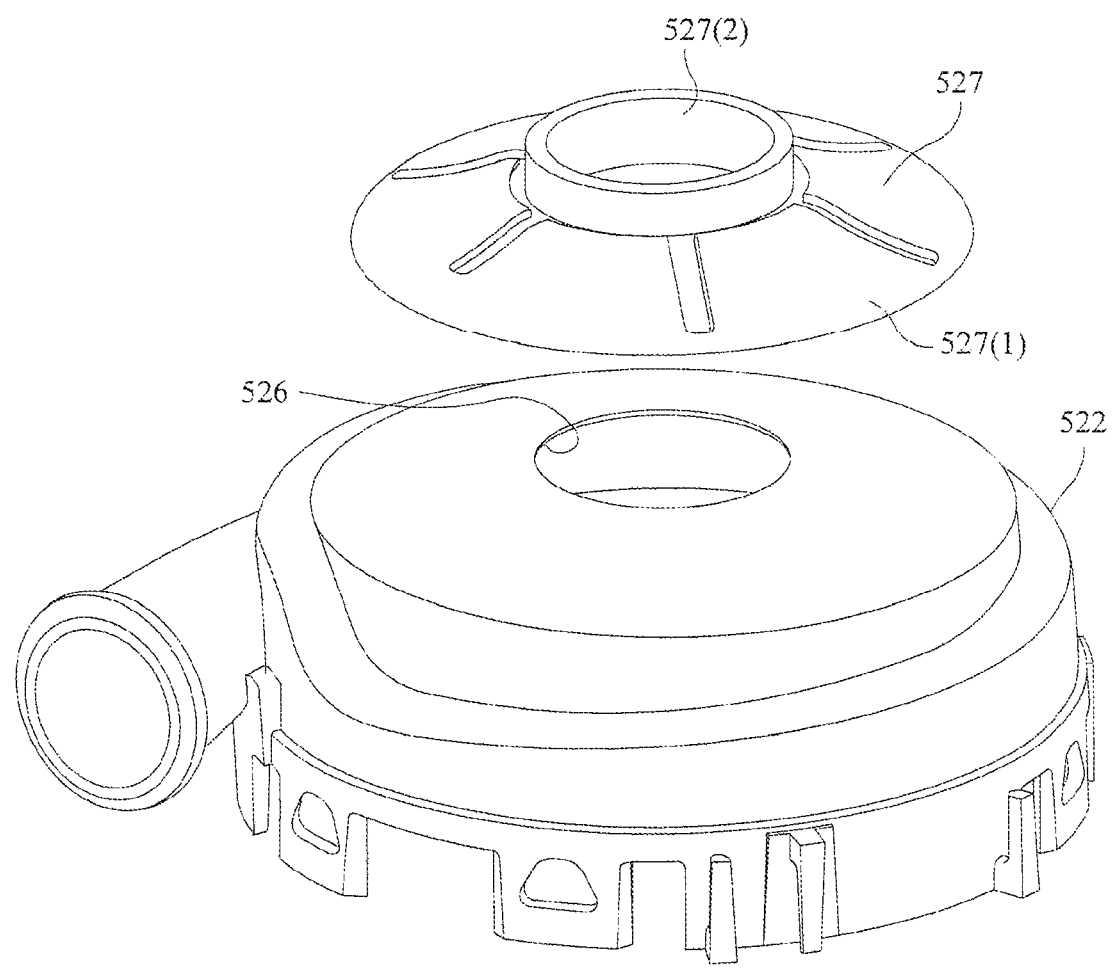
FIG. 22 is an exploded view of the first housing part and chimney of the blower of FIG. 18.
Figure 33:
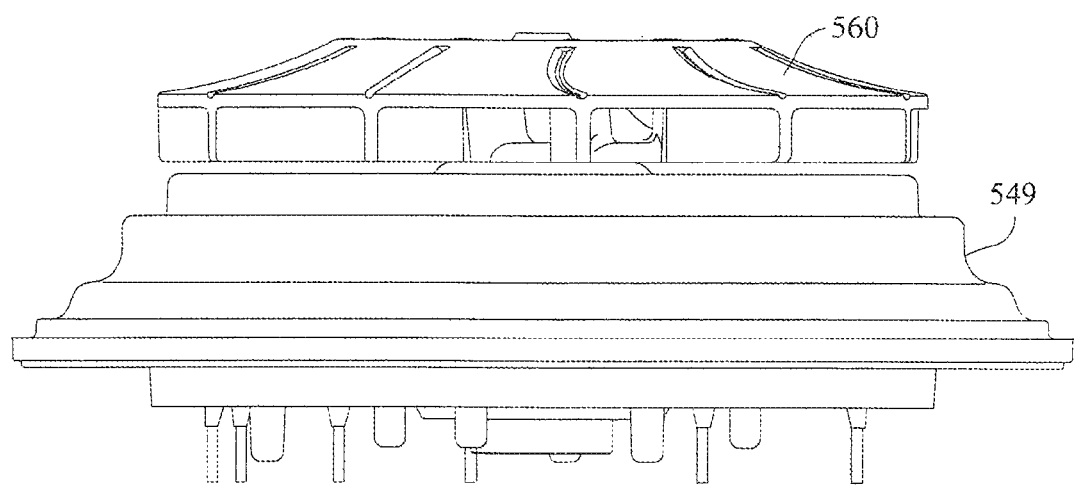
FIGS. 33 and 34 are side views showing the overmolded stationary component and stator assembly along with the impeller of the blower of FIG. 18.
Figure 34:
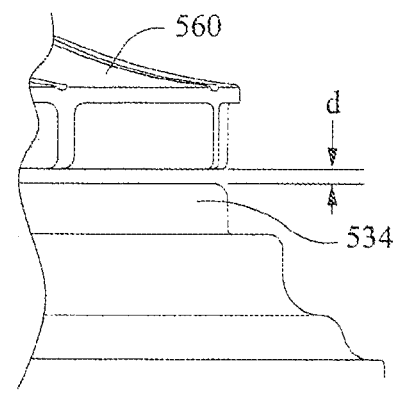

FIGS. 33 and 34 show the impeller 560 assembled to the assembly of the shaft assembly 551 and overmolded stationary assembly 549. In an example, as shown in FIG. 34, the spacing d between the impeller 560 and the shield portion 534 of the overmolded stationary assembly 549 may be about 0.5 to 1.0 mm, e.g., about 0.7 mm Seal In an example, as shown in FIGS. 20 and 21, a seal 595 (e.g., constructed of silicone rubber or other suitable material) is provided to the overmolded stationary assembly 549 to (i) provide a seal along the volute (i.e., stator airpath seal), (ii), support the PCBA 590, and (iii) provide a wire grommet for guiding wires from the PCBA to external the blower.

Figure 35:
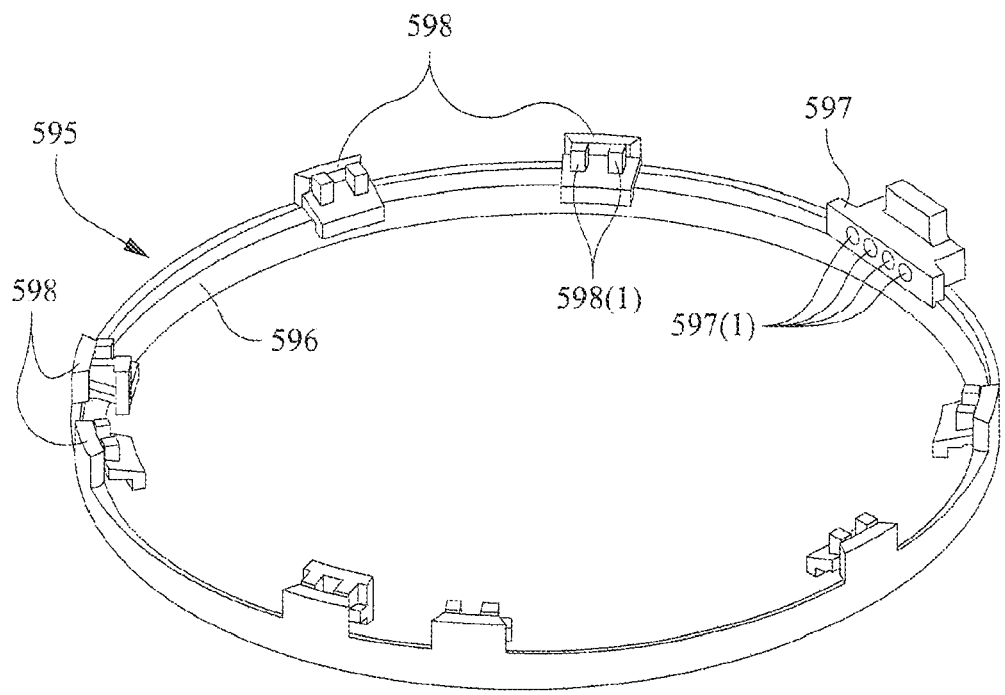
FIG. 35 is a perspective view of a seal for the PCBA of the blower of FIG. 18.

As shown in FIG. 35, the seal 595 includes a ring-shaped main body 596 with an integrated wire grommet 597 and integrated tab members 598. In an example, the seal is integrally molded in one piece, e.g., constructed of silicone rubber or other suitable material.

Figure 38:
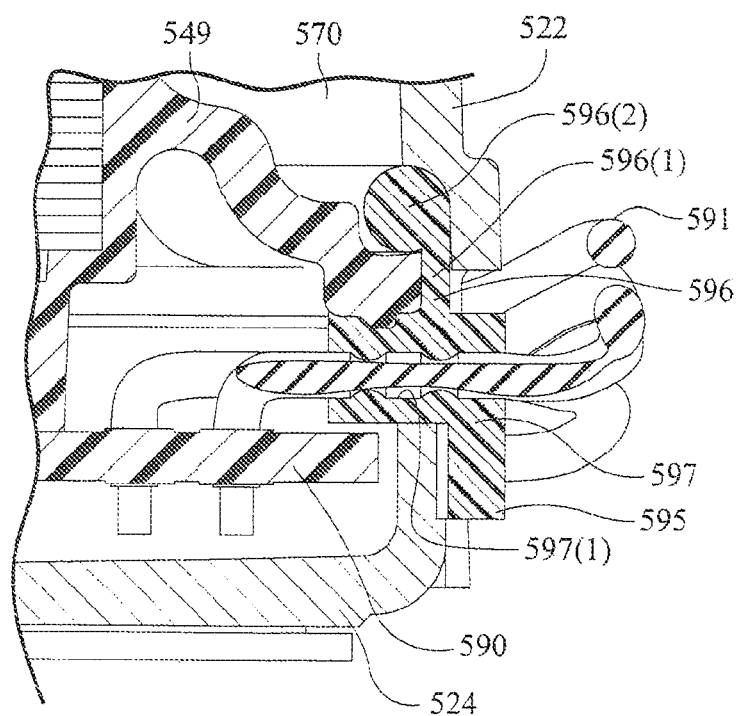
FIGS. 38 and 39 are cross-sectional views showing the seal install and wire routing of the PCBA of the blower of FIG. 18.
Figure 39:
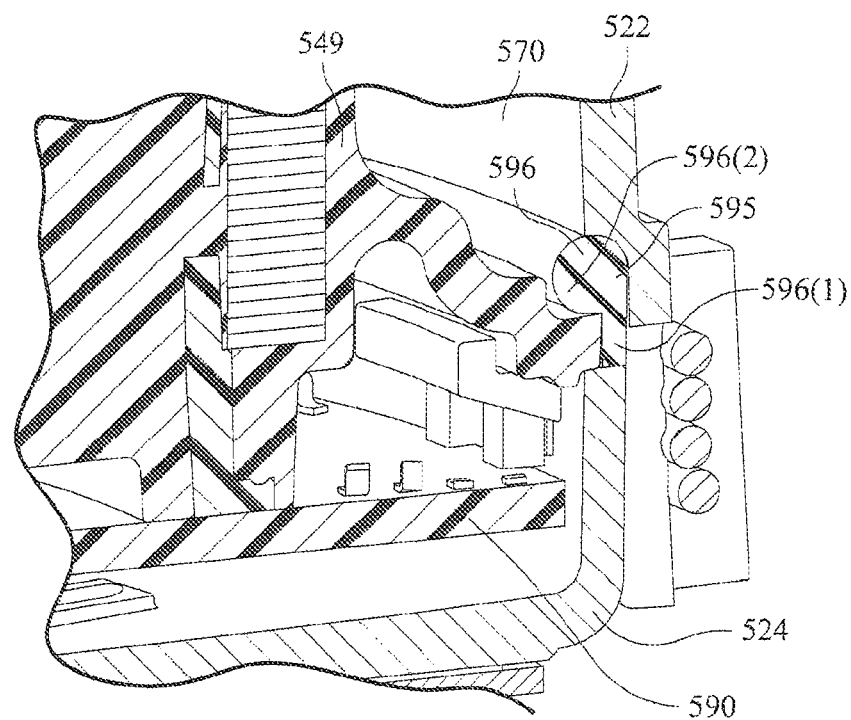

As best shown in FIGS. 20, 38, and 39, the main body 596 includes a side wall portion 596(1) and a bulbous end portion 596(2) that are positioned between the first housing part 522 and the overmolded stationary assembly 549 to provide a seal along the volute 570 defined between such components.

Figure 36:
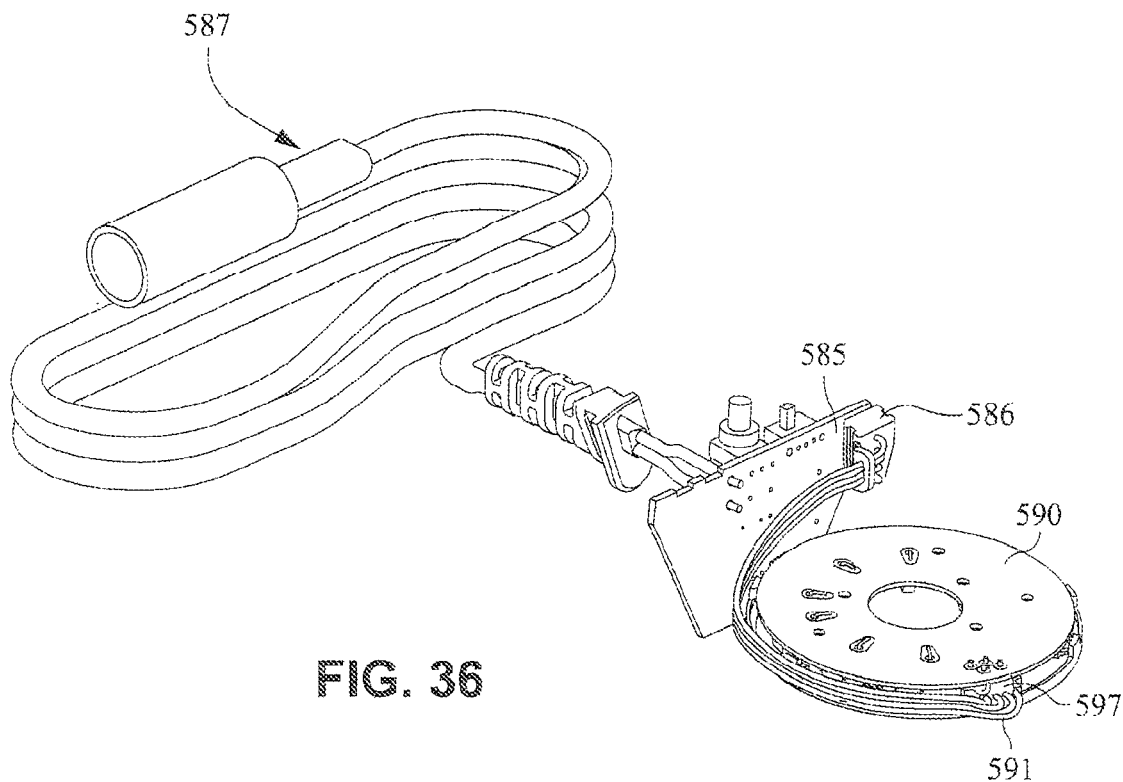
FIG. 36 is a perspective view of the PCBA of the blower of FIG. 18.
Figure 37:
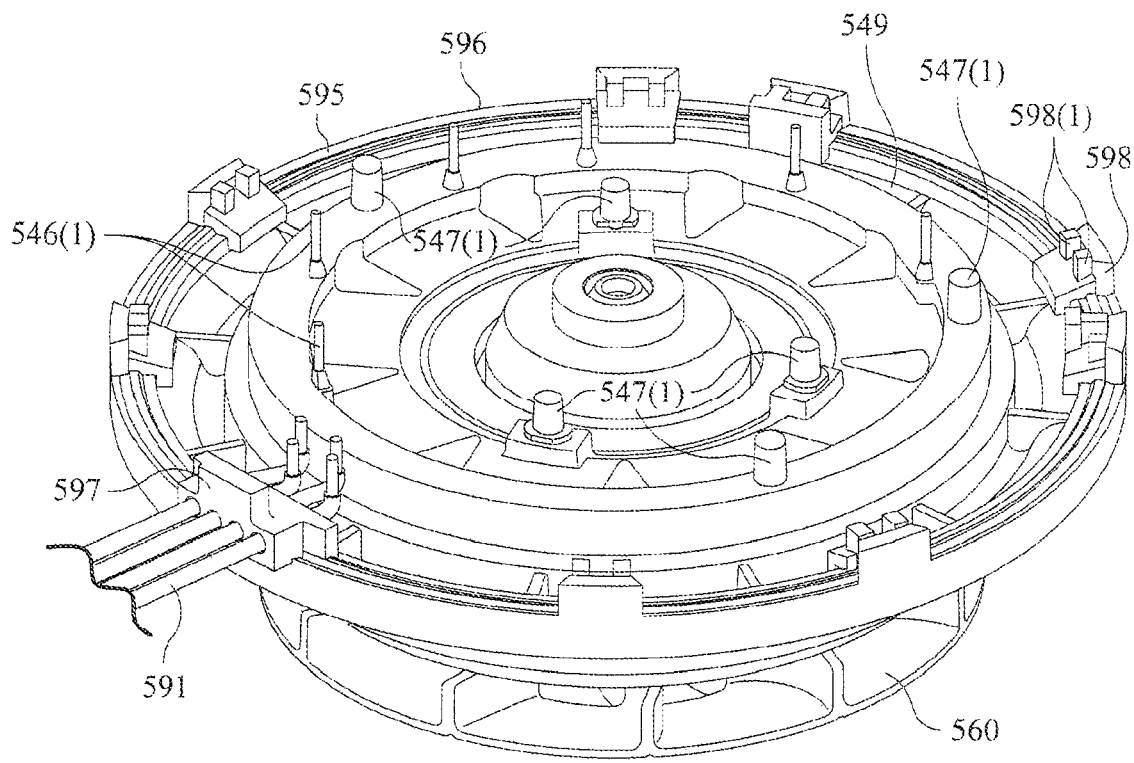
FIG. 37 is a perspective view showing installation of the seal of FIG. 35 to the overmolded stationary component and stator assembly.
Figure 40:
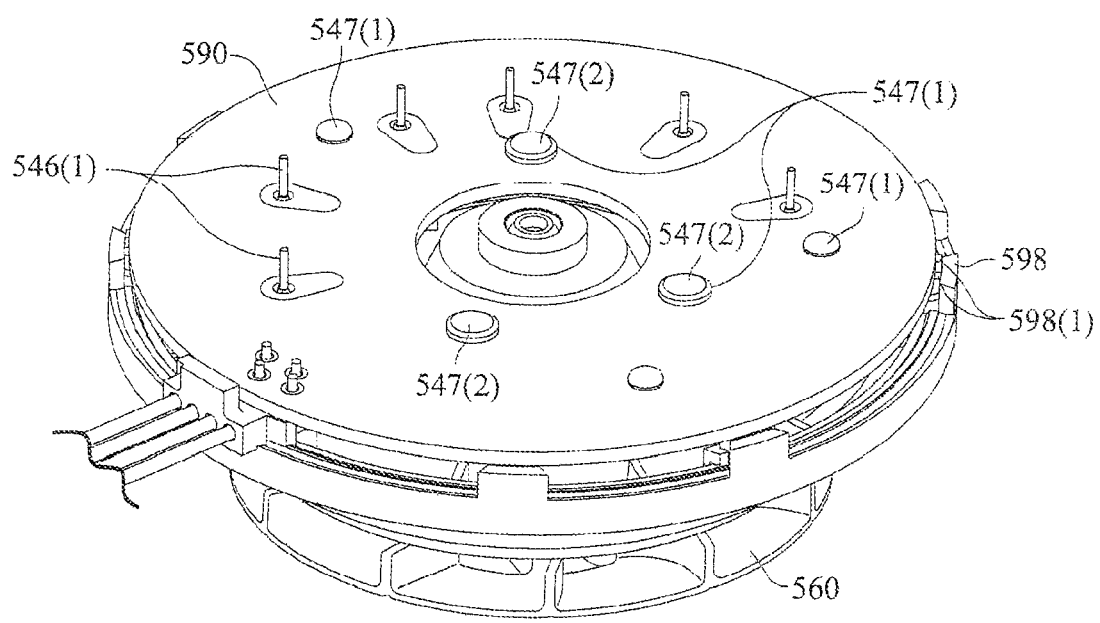
FIG. 40 is a perspective view showing heat staking assembly of the PCBA of the blower of FIG. 18.

The tab members 598 include support arms 598(1) to support the PCBA 590, e.g., see FIGS. 37 and 40. As shown in FIGS. 35, 36, and 38, the wire grommet 597 includes openings 597(1) (e.g. four openings as illustrated, however more or less openings are possible depending on application) for routing or guiding wires 591 from the PCBA 590 to outside the blower.

PCBA

As shown in FIG. 36, the PCBA 590 is coupled to a satellite PCBA 585 by wires 591, which satellite PCBA 585 is coupled to an overmolded power cord assembly 587. A grommet 586 with a living hinge is provided to the satellite PCBA 585 to couple the wires 591 to the satellite PCBA 585. The satellite PCBA 585 may provide additional elements to assist in controlling the motor. PCBA 585 provides a user adjustable interface to permit the selection of a speed corresponding with a given output pneumatic pressure; protects the PCBA 590 from energy surges that may manifest on the power lines; and/or allows for calibration adjustments, if needed, during final production processes.

Seal and PCBA Installation

FIGS. 37 and 40-48 show installation of the seal 595 and PCBA 590 to the overmolded stationary assembly 549, and the subsequent installation to the housing 520.

As shown in FIG. 37, the seal 595 is first installed to the overmolded stationary assembly 549. As illustrated, the main body 596 of the seal 595 wraps around the outer edge of the assembly 549 and the wire grommet 597 and tab members 598 engage along an upwardly facing lip of the assembly 549 (as viewed in FIG. 37).

The PCBA 590 is then installed to the seal 595. As shown in FIGS. 37 and 40, the overmolded stationary assembly 549 includes a plurality of pin-type mounting protrusions 547(1) (provided by the insulator 547 of the integrated stator assembly 544 described above) that are adapted to engage within corresponding holes provided in the PCBA 590. The protrusions and holes are positioned to precisely position and align the PCBA 590 and its attendant components accurately with respect to the assembly 549 and its integrated stator assembly.

Also, the overmolded stationary assembly 549 includes a plurality of wires 546(1) (provided by windings 546 of the integrated stator assembly 544 described above) that are adapted to extend through corresponding holes provided in the PCBA 590.

Figure 41:
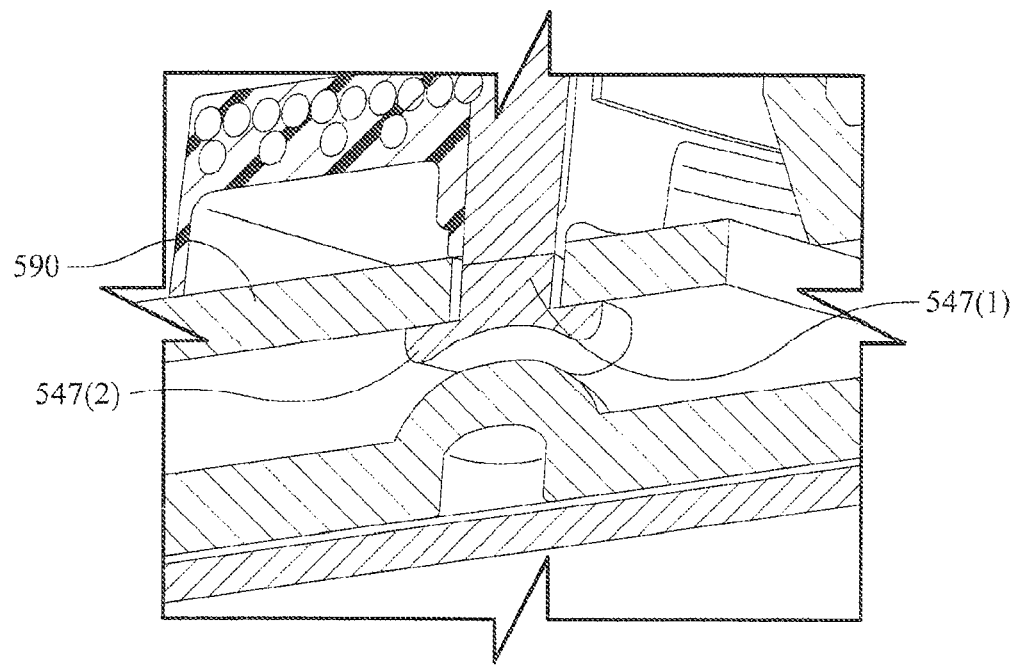
FIGS. 41 and 42 are cross-sectional views showing heat staking assembly of the PCBA of the blower of FIG. 18.
Figure 42:
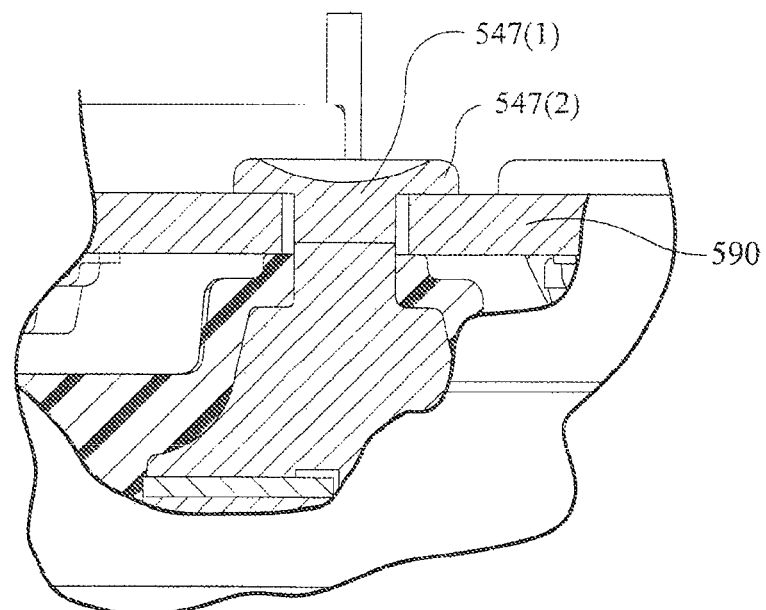

Then, as shown in FIGS. 40-42, the arrangement is processed to form heads 547(2) on the tips of one or more of the protrusions 547(1), e.g., using heat staking. This forms the protrusions 547(1) into rivets to securely mount the PCBA 590 to the assembly 549.

Figure 43:
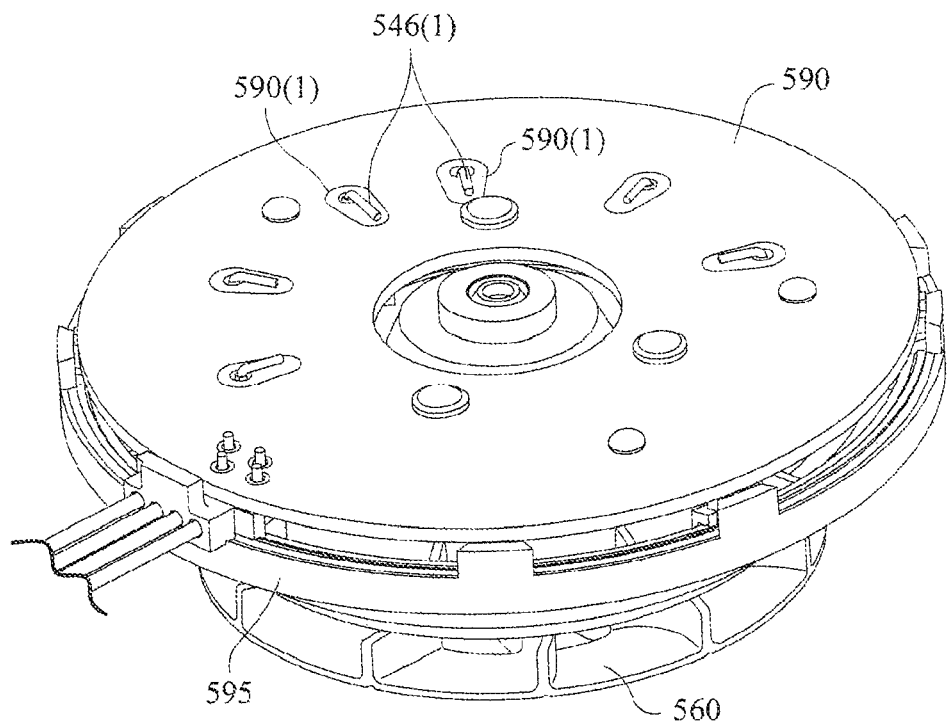
FIG. 43 is a perspective view showing soldering of the PCBA of the blower of FIG. 18.
Figure 44:
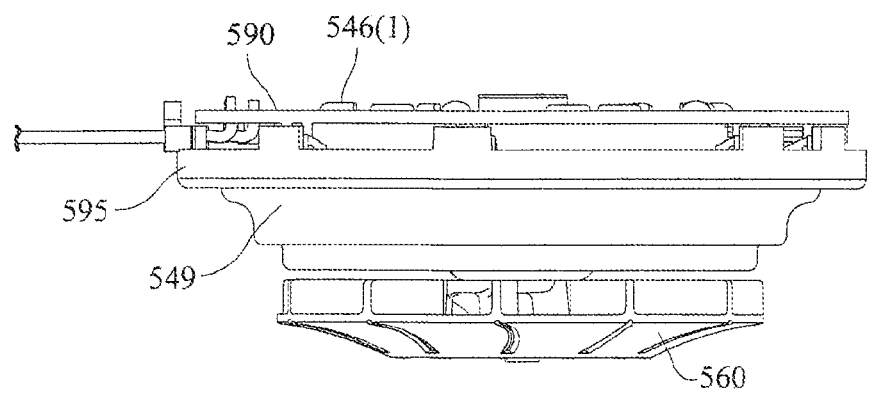
FIG. 44 is a side view showing soldering of the PCBA of the blower of FIG. 18.

Also, as shown in FIGS. 43 and 44, the ends of the wires 546(1) are bent and connected, e.g., by soldering, to the PCBA 590. A soldering surface 590(1) (e.g., gold surface) may be provided around each wire opening of the PCBA to facilitate connection of wire to the PCBA.

Figure 45:
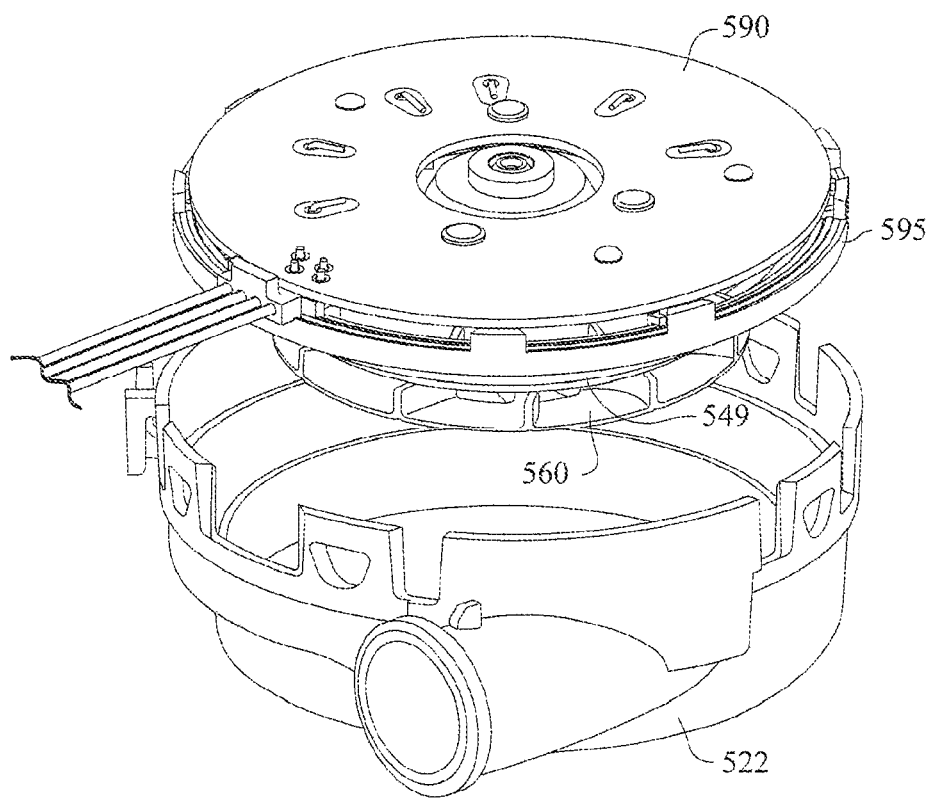
FIG. 45 is a perspective view showing assembly of the built stationary component/PCBA to the first housing part of the blower of FIG. 18.
Figure 46:
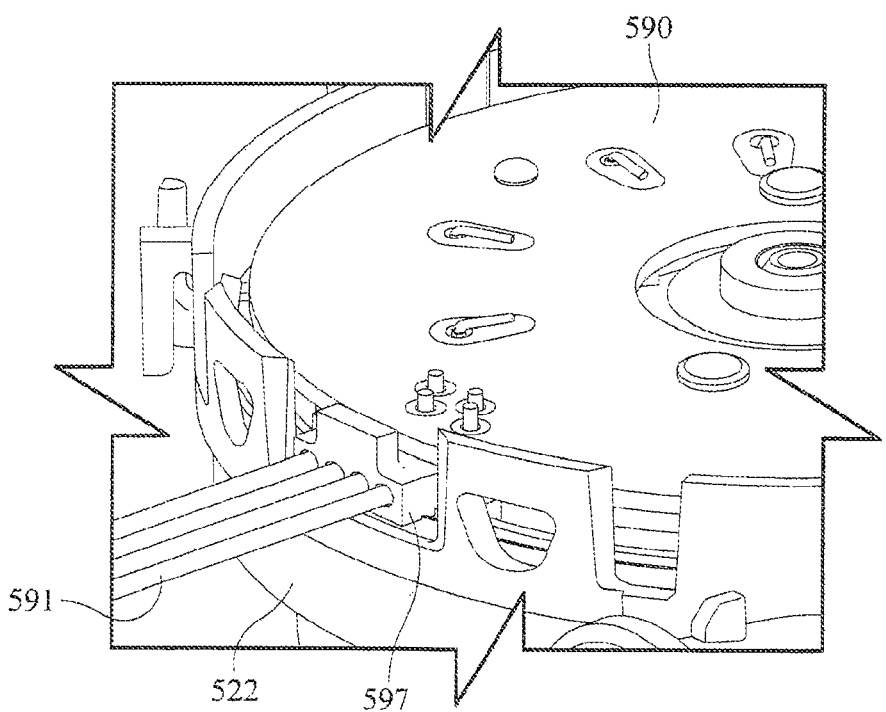
FIG. 46 is a perspective view of the built stationary component/PCBA assembled to the first housing part of the blower of FIG. 18.
Figure 47:
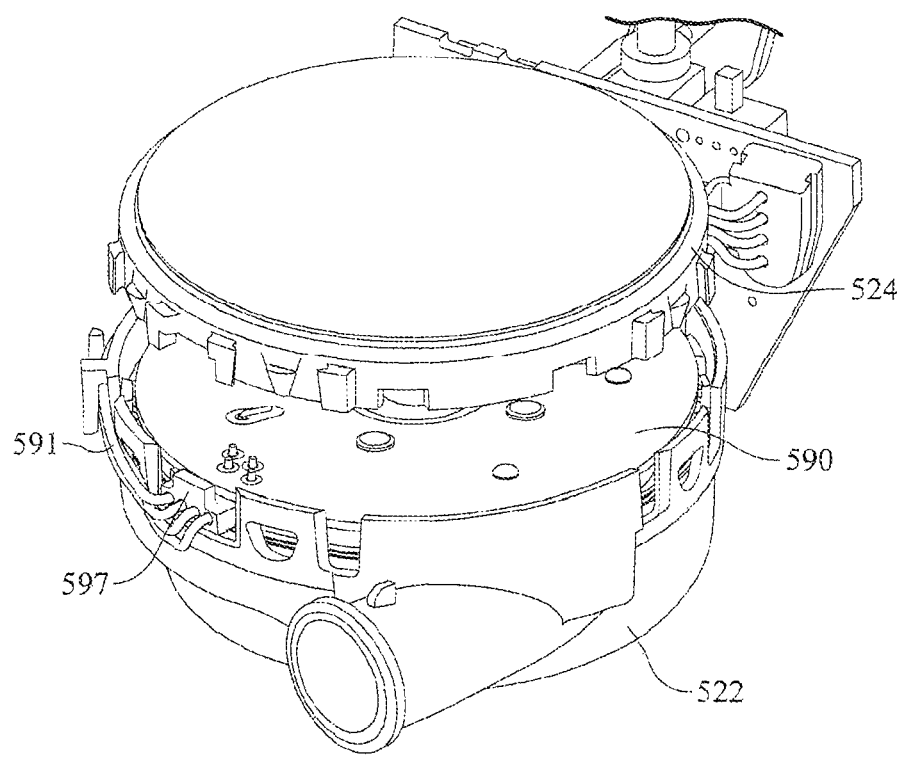
FIG. 47 is a perspective view showing assembly of the second housing part to the assembled components of FIGS. 45 and 46.
Figure 48:
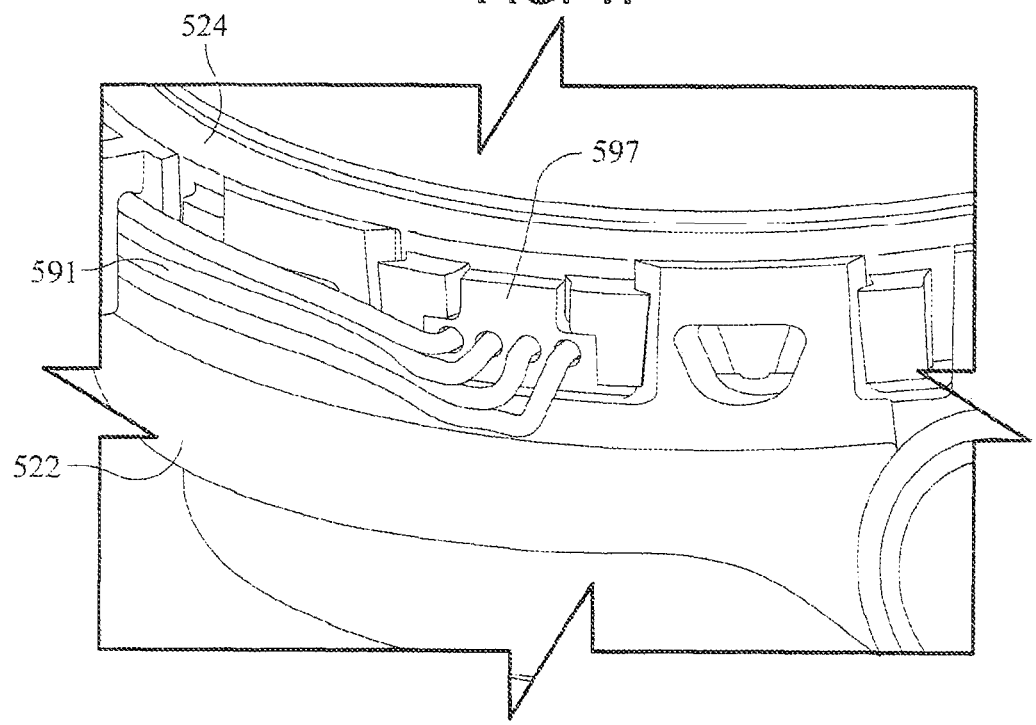
FIG. 48 is a perspective view showing the second housing part assembled to the assembled components of FIGS. 45 and 46.

FIGS. 45 and 46 show assembly of the built stationary component/PCBA to the first housing part 522, and FIGS. 47 and 48 show the subsequent assembly of the second housing part 524 to the first housing part 522. FIGS. 46 and 48 are enlarged views showing positioning and support of the wire grommet 597 with respect to the first and second housing parts.

Blower within Casing of PAP Device

Figure 49:
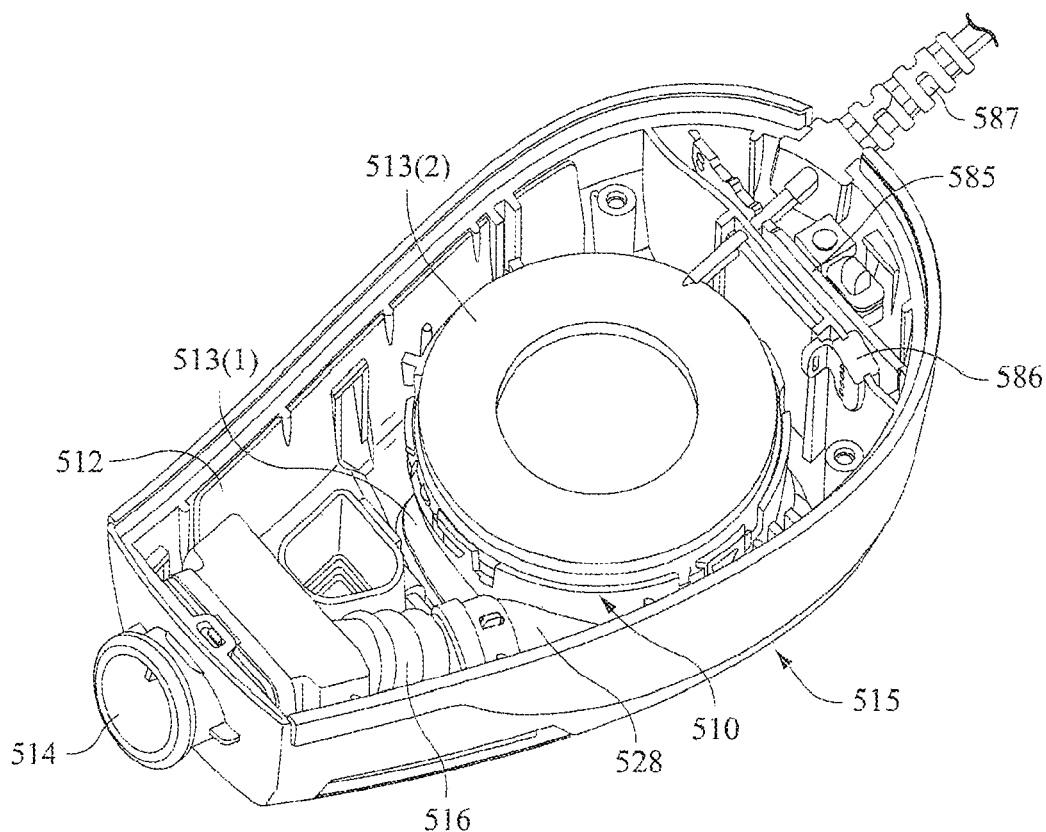
FIG. 49 is a perspective view showing the blower of FIG. 18 mounted within the casing of a PAP device according to an example of the disclosed technology, the casing shown with no cover.
Figure 50:
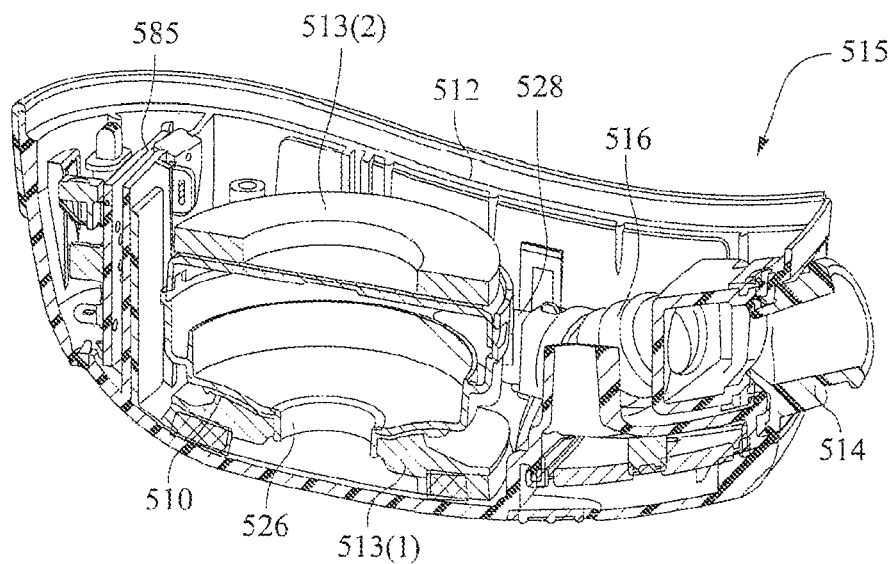
FIG. 50 is a cross-sectional view of the blower and casing of FIG. 49.
Figure 51:
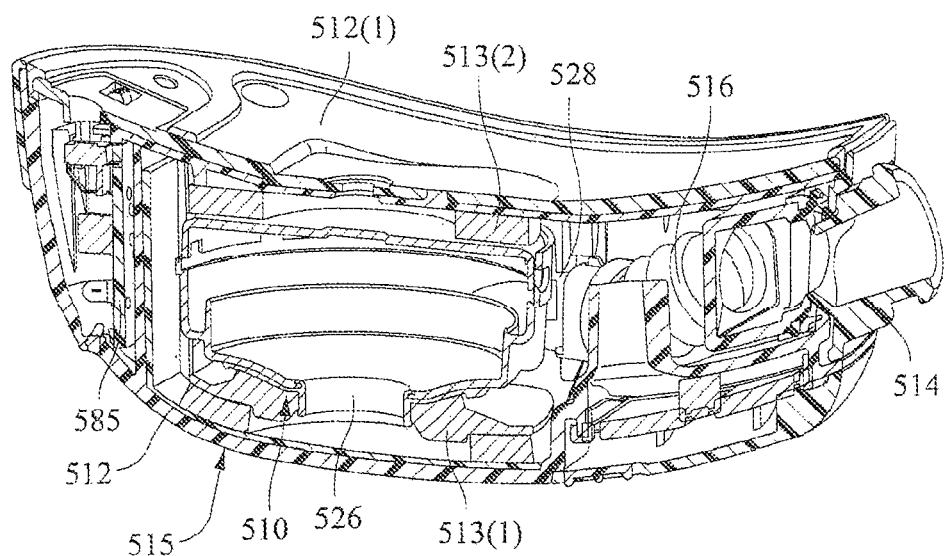
FIG. 51 is a cross-sectional view of the blower and casing of FIG. 49, the casing shown with a cover.
Figure 52:
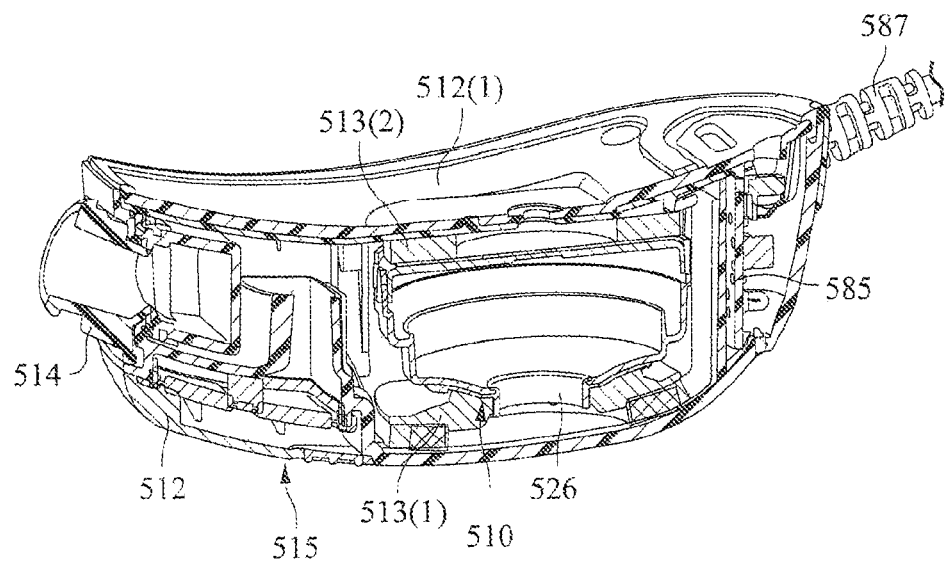
FIG. 52 is another cross-sectional view of the blower and casing of FIG. 49, the casing shown with a cover.

FIGS. 49 to 52 show the blower 510 mounted within the casing 512 of a PAP device 515 according to an example of the disclosed technology. FIGS. 49 and 50 show the casing with a removable cover or end wall removed, and FIGS. 51 and 52 show the casing 512 with the cover 512(1) installed.

As illustrated, the blower 510 is supported within the casing 512. Insulators 513(1), 513(2) may be provided to respective ends of the blower to stably support the blower within the casing and absorb vibrations/noise from the blower in use.

The blower 510 is operable to draw a supply of air into its inlet 526 through one or more intake openings provided in the casing and provide a pressurized flow of air at an its outlet 528. The blower outlet 528 is coupled to the outlet 514 of the casing 512 by a flexible tube member 516.

As illustrated, the internal wall structure of the casing 512 is structured to support the satellite PCBA 585 and power cord assembly 587 associated with the PCBA 590 of the blower 510.

2. Blower with Silicone Bladder

Figure 5:
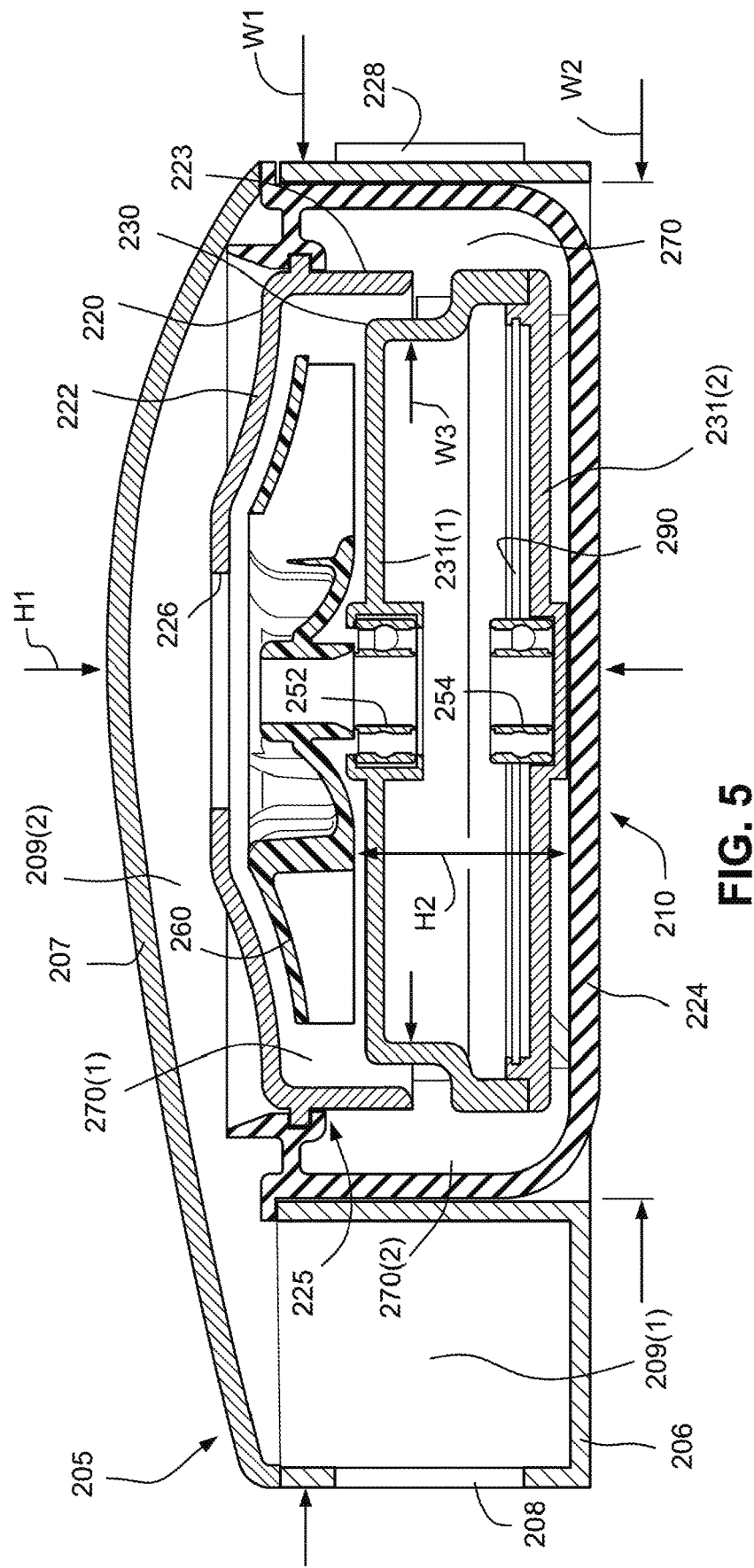
FIG. 5 is a cross-sectional view of a blower according to another example of the disclosed technology.

FIG. 5 illustrates a blower 210 according to another example of the technology. In this example, a portion of the housing is formed of silicone which acts as a vibration isolator and outlet muffler in use.

The blower 210 includes a housing 220 with first and second housing parts 222, 224, a stationary component 230, a motor positioned within the stationary component 230 and adapted to drive a rotatable shaft or rotor (not shown), a PCBA 290 for motor control, and an impeller 260 provided on one side of the stationary component 230 and adapted to be coupled to an end portion of the rotor. In addition, the blower includes an outer housing structure 205 communicated with the inlet 226 and structured to act as a muffler for incoming air.

In the illustrated example, the first housing part 222 provides the inlet 226 and the second housing part 224 provides the outlet 228. The first housing part 222, second housing part 224, and stationary component 230 cooperate to define the volute 270 that directs air towards the outlet. Also, the first housing part 222 provides the separating wall 223 that separates the volute 270 into two regions, i.e., the high speed airpath region 270(1) and the low speed airpath region 270(2) as described above. The first and second housing parts 222, 224 may provide a joint 225 (e.g., tongue and groove arrangement or a welded connection) to facilitate alignment and connection.

Moreover, the second housing part 224 (which provides an exterior portion, outer wall portion, or pressure side of the volute) is formed of an elastomer material, e.g., silicone or TPE. This arrangement allows the second housing part 224 to act as an air cushion in use, e.g., second housing part may at least partially inflate when pressurized in use. In use, the silicone second housing part 224 supports the first housing part 222, stationary component 230, motor, and impeller 260 in a flexible, vibration-isolated manner Thus, vibrations and/or other movement generated by these components in use are substantially isolated, e.g., from the outer housing structure 205. Moreover, the silicone second housing part 224 acts a muffler for air exiting the outlet 228 in use.

In the illustrated example, the stationary component 230 includes first and second parts 231(1), 231(2) that are coupled to one another, e.g., by a joint. The first and second parts cooperate to define a hollow interior adapted to support and maintain the motor and rotor in an operative position. Also, the first and second parts of the stationary component are structured to retain bearings 252, 254 that rotatably support the rotor. For example, the first part 231(1) may include a recess for supporting one bearing 252 and the second part 231(2) may include a recess for supporting the other bearing 254. The first and second parts may be structured to support bearings of the same or mixed bearing sizes. In addition, the first part provides an opening along its axis that allows the end portion of the rotor to pass therethrough for engagement with the impeller 260.

The outer housing structure 205 includes a base 206 that extends around the exterior of the second housing part 224, and a cover 207 that encloses the top of the blower including the inlet 226. The base 206 provides an inlet 208 with an inlet chamber 209(1) to reduce at least a portion of the noise produced by the blower and radiated from the air inlet. In addition, the cover 207 provides a small chamber 209(2) upstream from the inlet chamber to muffle noise entering the inlet 226.

In an example, isolating foam or gels may also be used in one or more portions of the blower to muffle noise and vibration.

In an example, the blower may be structured to provide pressurized air in the range of 12-14 cmH$_2$O, about 25000 rpm, and flow rate of about 80-100 L/min.

In an example, as shown in FIG. 5, H1 may be about 30-35 mm (e.g., less than 35 mm, 31 mm), H2 may be about 10-20 mm (e.g., less than 20 mm, 14 mm, 18 mm), W1 may be about 80-90 mm (e.g., less than 90 mm, 83 mm), W2 may be about 65-75 mm (e.g., less than 75 mm, 69 mm), and W3 may be about 40-50 mm (e.g., less than 50 mm, 44 mm, 41 mm). However, other suitable dimensions are possible.

While the technology has been described in connection with several examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., one or more aspects of one example may be combined with one or more aspects of another example to realize yet other examples. Further, each independent feature or component of any given assembly may constitute an additional example. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A CPAP system for delivery of a flow of breathable gas at a continuously positive pressure to a patient for treatment of sleep disordered breathing, the CPAP system comprising:
    a PAP device including a blower structured to generate the flow of breathable gas at the continuously positive pressure,
    the blower comprising:
        a housing including an inlet and an outlet;
        a stationary component provided to the housing;
        an impeller positioned between the inlet of the housing and the stationary component; and
        a motor adapted to drive the impeller,
    wherein the housing and the stationary component cooperate to form a volute that directs the flow of breathable gas towards the outlet, wherein at least an outer wall portion of the housing forming the volute comprises a flexible elastomeric material,
    wherein the outer wall portion comprising the flexible elastomeric material provides an exterior portion or pressure side of the volute, and the outer wall portion is structured and arranged to at least partially inflate when pressurized in use,
    wherein the outlet of the housing of the blower is adapted to be in fluid communication with a patient interface, the patient interface including a sealing arrangement adapted to form a seal with a patient's nose and/or mouth.

2. The CPAP system according to claim 1, wherein the motor includes a stator assembly adapted to drive a rotor, and the impeller is coupled to an end portion of the rotor.

3. The CPAP system according to claim 2, wherein the rotor is supported by a pair of bearings, the pair of bearings supported by the stationary component.

4. The CPAP system according to claim 2, wherein the stator assembly is mounted in the stationary component.

5. The CPAP system according to claim 1, further comprising a printed circuit board assembly to control the motor mounted to the stationary component.

6. The CPAP system according to claim 1, wherein the blower is structured to provide pressurized gas in a range of 2-30 cmH$_2$O.

7. The CPAP system according to claim 1, wherein the blower includes a height less than about 35 mm and a width less than about 75 mm.

8. The CPAP system according to claim 1, wherein the outer wall portion of the housing forming the volute comprises a silicone material.

9. The CPAP system according to claim 1, further comprising an outer housing structure communicated with the inlet and structured to act as a muffler for incoming gas.

10. The CPAP system according to claim 1, wherein the housing includes a first housing part providing the inlet and a second housing part providing the outlet.

11. The CPAP system according to claim 10, wherein the second housing part comprises the outer wall portion comprising the flexible elastomeric material.

12. The CPAP system according to claim 11, wherein the second housing part is structured and arranged to support the first housing part, the stationary component, the impeller, and the motor in a flexible, vibration-isolated manner.

13. The CPAP system according to claim 11, wherein the second housing part is structured and arranged to act as a muffler for gas exiting the outlet in use.

14. The CPAP system according to claim 1, wherein the housing includes a first housing part providing the inlet and a second housing part providing the outlet, wherein the second housing part comprises the flexible elastomeric material, and wherein the first housing part comprises a different material than the second housing part.

15. The CPAP system according to claim 14, wherein the first housing part comprises a relatively rigid material.

16. The CPAP system according to claim 15, wherein the first housing part comprises metal or plastic.

* * * * *